United States Patent
Nakazawa et al.

(10) Patent No.: US 10,362,939 B2
(45) Date of Patent: Jul. 30, 2019

(54) FUNDUS ANALYSIS APPARATUS AND FUNDUS OBSERVATION APPARATUS

(71) Applicants: TOHOKU UNIVERSITY, Sendai-shi (JP); KABUSHIKI KAISHA TOPCON, Itabashi-ku (JP)

(72) Inventors: Toru Nakazawa, Sendai (JP); Kazuko Omodaka, Sendai (JP); Akiko Matsumoto, Asaka (JP); Tsutomu Kikawa, Adachi-ku (JP); Masahiro Akiba, Toda (JP)

(73) Assignees: TOHOKU UNIVERSITY, Sendai-shi (JP); KABUSHIKI KAISHA TOPCON, Itabashi-ku (JP)

( * ) Notice: Subject to any disclaimer, the term of this patent is extended or adjusted under 35 U.S.C. 154(b) by 134 days.

(21) Appl. No.: 15/509,421

(22) PCT Filed: Aug. 28, 2015

(86) PCT No.: PCT/JP2015/074491
§ 371 (c)(1),
(2) Date: Mar. 7, 2017

(87) PCT Pub. No.: WO2016/039188
PCT Pub. Date: Mar. 17, 2016

(65) Prior Publication Data
US 2017/0273557 A1    Sep. 28, 2017

(30) Foreign Application Priority Data
Sep. 8, 2014   (JP) .................................. 2014-182326

(51) Int. Cl.
G06K 9/00   (2006.01)
A61B 3/12   (2006.01)
(Continued)

(52) U.S. Cl.
CPC .......... *A61B 3/1225* (2013.01); *A61B 3/0025* (2013.01); *A61B 3/0033* (2013.01);
(Continued)

(58) Field of Classification Search
None
See application file for complete search history.

(56) References Cited

U.S. PATENT DOCUMENTS

| 2011/0170062 A1 | 7/2011 | Isogai et al. |
| 2012/0127428 A1 | 5/2012 | Isogai et al. |

(Continued)

FOREIGN PATENT DOCUMENTS

| JP | 2011-45675 A | 3/2011 |
| JP | 2012-100811 A1 | 5/2012 |

(Continued)

OTHER PUBLICATIONS

International Search Report dated Nov. 17, 2015, in PCT/JP2015/074491 filed Aug. 28, 2015.

(Continued)

*Primary Examiner* — Wei Wen Yang
(74) *Attorney, Agent, or Firm* — Oblon, McClelland, Maier & Neustadt, L.L.P.

(57) ABSTRACT

A fundus analysis apparatus includes a storage, an area setting unit, and a morphological information generating unit. The storage is configured to store OCT information acquired by applying optical coherence tomography to the fundus of an eye. The area setting unit is configured to set a front area corresponding to a front surface of the lamina cribrosa and a rear area corresponding to a rear surface of the lamina cribrosa in the OCT information. The morphological information generating unit is configured to generate morphological information indicating the morphology of the lamina cribrosa based on at least the front area and the rear area.

12 Claims, 10 Drawing Sheets

(51) Int. Cl.
    A61B 3/00    (2006.01)
    A61B 3/10    (2006.01)
    G06T 7/00    (2017.01)
    G06T 11/00   (2006.01)
    G06T 7/62    (2017.01)
(52) U.S. Cl.
    CPC ............ *A61B 3/0041* (2013.01); *A61B 3/102* (2013.01); *G06T 7/0012* (2013.01); *G06T 7/62* (2017.01); *G06T 11/003* (2013.01); *G06T 2207/10016* (2013.01); *G06T 2207/10101* (2013.01); *G06T 2207/20036* (2013.01); *G06T 2207/20056* (2013.01); *G06T 2207/20104* (2013.01); *G06T 2207/30041* (2013.01)

(56) References Cited

U.S. PATENT DOCUMENTS

| | | |
|---|---|---|
| 2012/0194782 A1 | 8/2012 | Imamura |
| 2013/0093870 A1* | 4/2013 | Shibutani ............... A61B 3/102 |
| | | 348/78 |
| 2013/0194546 A1 | 8/2013 | Iwase |
| 2014/0362344 A1 | 12/2014 | Imamura |
| 2016/0019691 A1* | 1/2016 | Imamura ................... G06T 5/50 |
| | | 382/128 |

FOREIGN PATENT DOCUMENTS

| | | |
|---|---|---|
| JP | 2012-115575 A | 6/2012 |
| JP | 2012-157591 A | 8/2012 |
| JP | 2012-161426 A | 8/2012 |
| JP | 2013-153844 A | 8/2013 |

OTHER PUBLICATIONS

Omodaka et al., "Correlation between morphology of optic disc determined by Heidelberg Retina Tomograph II and visual function in eyes with open-angle glaucoma", Clinical Ophthalmology, (Jul. 10, 2010), pp. 765-772.

Inoue et al., "Three-dimensional High-speed Optical Coherence Tomography Imaging of Lamina Cribrosa in Glaucoma", American Academy of Ophthalmology, (2009), vol. 116, No. 2, pp. 214-222.

* cited by examiner

FUNDUS ANALYSIS APPARATUS AND FUNDUS OBSERVATION APPARATUS

TECHNICAL FIELD

Embodiments described herein relate generally to a fundus analysis apparatus and a fundus observation apparatus that analyze information on the fundus acquired by using optical coherence tomography (OCT).

BACKGROUND ART

Glaucoma is one of the leading causes of adult blindness, and visual impairment in glaucoma is irreversible. Therefore, it is desired that the diagnosis of glaucoma and the observation of the progression thereof be properly carried out. OCT techniques for forming an image representing the surface morphology and the internal morphology of a measurement object by using a light beam from a laser light source or the like are useful for the diagnosis of glaucoma and the like. For example, with reference to an image of the fundus formed by using OCT, changes in the morphology of the retina can be observed. Thus, the progression of glaucoma, the posttreatment condition, and the like can be observed.

In the diagnosis of glaucoma and the like, it is considered to be important to focus attention on changes in the morphology of the optic disc and that of the retinal nerve fiber layer. As to the optic disc, the shape and size are of interest, and the inclination of the optic disc, and the shape and size of C (Cup), D (Disc), and R (Rim) and the like are used for diagnostic materials. Meanwhile, as to the retinal nerve fiber layer, the thickness, loss, and the like are used for diagnostic materials. In addition to these, in recent years, as contributing to the early detection of glaucoma, the morphology of the lamina cribrosa has been attracting attention. The lamina cribrosa is a mesh-like tissue in which a plurality of holes is formed where the optic nerves in the optic disc pass through.

For example, the patent document 1 discloses the analysis of a lamina cribrosa region. Specifically, the patent document 1 discloses a method of detecting the lamina cribrosa region from a tomographic image obtained by using OCT and of analyzing a lamina cribrosa region.

PRIOR ART DOCUMENT

[Patent Document]
[Patent Document 1] Japanese Unexamined Patent Publication No. 2013-153844

SUMMARY OF THE INVENTION

Problems to be Solved by the Invention

In recent years, it has been confirmed that the shape of the optic disc is significantly correlated to the classification and severity of glaucoma (Kazuko Omodaka, et al., "Correlation between morphology of optic disc determined by Heidelberg Retina Tomograph II and visual function in eyes with open-angle glaucoma", 2010, Clinical Ophthalmology, pp. 765-772), and evidence is obtained for realizing the presymptomatic diagnosis of glaucoma. In this way, as the study on the relationship between the glaucoma and the morphology of the fundus is progressing for realizing the presymptomatic diagnosis of glaucoma and the like, the acquisition of information about a portion of the fundus becomes more important.

However, it may sometimes be impossible to acquire information on the lamina cribrosa sufficient to realize the evaluation and diagnosis of glaucoma as well as presymptomatic diagnosis by only the analysis method disclosed in the patent document 1.

The present invention has been made to solve the above problems, and an object thereof is to provide a technology capable of acquiring new information on the lamina cribrosa.

Means of Solving the Problems

According to one embodiment, a fundus analysis apparatus includes: a storage configured to store OCT information acquired by applying optical coherence tomography to the fundus of an eye; an area setting unit configured to set a front area corresponding to a front surface of the lamina cribrosa and a rear area corresponding to a rear surface of the lamina cribrosa in the OCT information; and a morphological information generating unit configured to generate morphological information indicating the morphology of the lamina cribrosa based on at least the front area and the rear area.

Effects of the Invention

According to one embodiment, it is possible to acquire new information on the lamina cribrosa. By acquiring newly obtained information on the lamina cribrosa, it becomes possible to evaluate and diagnose glaucoma as well as to perform presymptomatic diagnosis more accurately.

MODES FOR CARRYING OUT THE INVENTION

Figure 1:
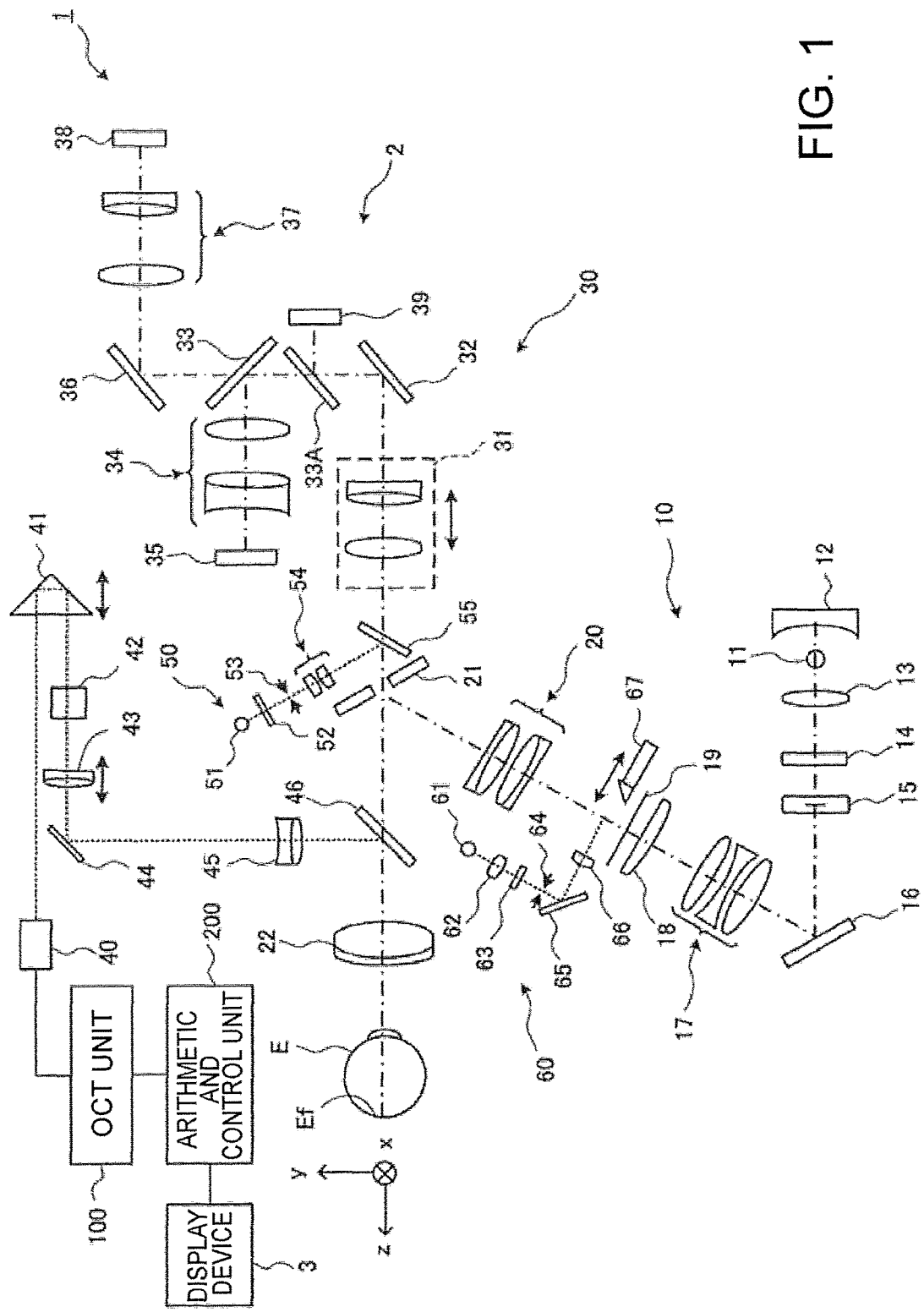
FIG. 1 is a schematic diagram illustrating an example of the configuration of a fundus observation apparatus according to an embodiment.

Referring now to the drawings, a detailed description is given of illustrative embodiments of the present invention. A fundus observation apparatus according to an embodiment obtains OCT information on the fundus by using OCT. Examples of the OCT information include: processing result of fast Fourier transform (FFT) based on a detection result obtained by a detector for detecting interference light by using OCT (e.g., detection signal from a CCD image sensor) (that is, information to be imaged); a tomographic image of the fundus obtained by using OCT, i.e., two-dimensional tomographic image, three-dimensional image, multi planar reconstruction (MPR) image, and the like. Further, having received the OCT information obtained using OCT, the fundus analysis apparatus according to an embodiment performs analysis process of the OCT information. Hereinafter an image acquired by using OCT may sometimes be referred to as "OCT image". In addition, measurement performed for obtaining the OCT information may sometimes be referred to as "OCT measurement". Incidentally, the disclosure of the documents cited herein may be incorporated in the following embodiments by reference.

While the following embodiment describes a configuration using Fourier-domain OCT, a fundus observation apparatus of the embodiment can acquire both OCT information (OCT image) of the fundus by using spectral-domain OCT and a fundus image. The embodiment can be applied to fundus observation apparatuses using other type of OCT than spectral-domain OCT, such as, for example, swept-source OCT. Further, an apparatus that combines the functions of an OCT device and a fundus camera is explained in the following embodiments; however, the OCT device having a configuration of an embodiment can be applied to other photographing devices than the fundus camera, such as a scanning laser ophthalmoscope (SLO), a slit lamp, an ophthalmic surgical microscope, or the like. Alternatively, the configuration of an embodiment can be applied to an (single-functional) OCT device.

In the following embodiments, a description is given of a case of using an OCT image captured of the fundus of the eye. Examples of the OCT image include an A scan image, a B-scan image, a front image, and the like. Examples of the front image include a C-scan image, a projection image, a flattened image, a shadowgram, and the like.

In addition, in the following embodiment, the lamina cribrosa (optic nerve lamina cribrosa) area is an image area corresponding to the lamina cribrosa. The lamina cribrosa is one of tissues that form the fundus. The lamina cribrosa includes at least a mesh-like portion having a plurality of holes where the optic nerves in the optic disc pass through.

[Configuration]

Figure 2:
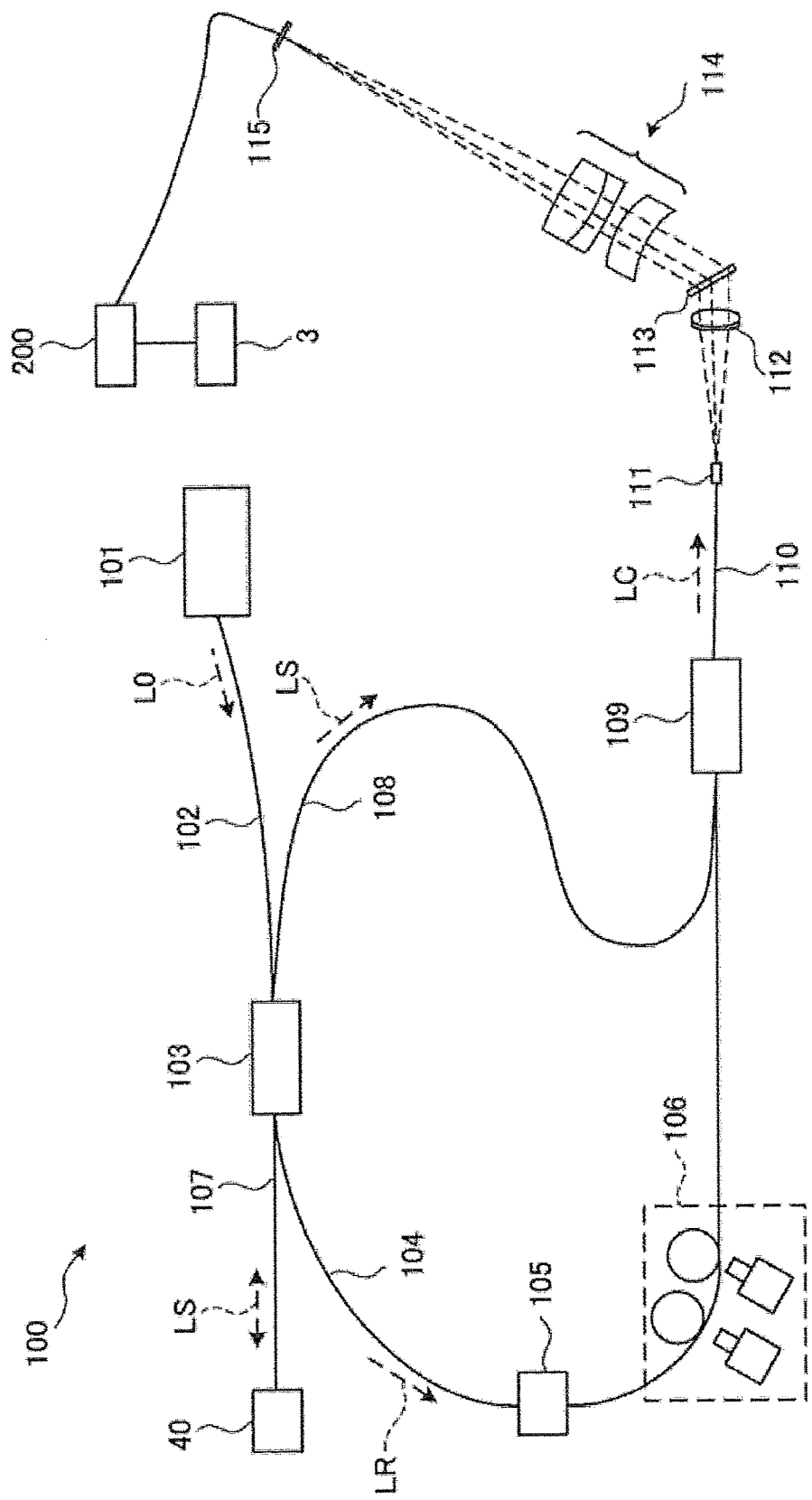
FIG. 2 is a schematic diagram illustrating an example of the configuration of the fundus observation apparatus of the embodiment.

As illustrated in FIGS. 1 and 2, a fundus observation apparatus 1 includes a fundus camera unit 2, an OCT unit 100, and an arithmetic and control unit 200. The fundus camera unit 2 has almost the same optical systems as a conventional fundus camera. The OCT unit 100 is provided with an optical system for obtaining an OCT image of the fundus. The arithmetic and control unit 200 is provided with a computer that performs various arithmetic processes, control processes, and the like. Further, the arithmetic and control unit 200 has functions as a "fundus analysis apparatus". The functions of the "fundus analysis apparatus" may be implemented by the arithmetic and control unit 200 and an operation unit 240B (described later).

[Fundus Camera Unit]

As illustrated in FIG. 1, the fundus camera unit 2 is provided with an optical system for forming a two-dimensional image (fundus image) representing the surface morphology of the fundus Ef of the subject's eye E. Fundus images include observation images, photographed images, and the like. The observation image is, for example, a monochrome moving image formed at a predetermined frame rate using near-infrared light. The photographed image may be, for example, a color image captured by flashing visible light or a monochrome still image using near-infrared light or visible light as illumination light. The fundus camera unit 2 may be configured to be capable of acquiring other types of images such as a fluorescein angiography image, an indocyanine green fluorescent image, and a fundus autofluorescent image.

The fundus camera unit 2 is provided with a jaw holder and a forehead rest for supporting the face of the subject. The fundus camera unit 2 is also provided with an illumination optical system 10 and an imaging optical system 30. The illumination optical system 10 irradiates illumination light to the fundus Ef. The imaging optical system 30 guides the illumination light reflected from the fundus to imaging devices (CCD image sensors 35 and 38, sometimes simply referred to as "CCD"). Further, the imaging optical system 30 guides signal light coming from the OCT unit 100 to the fundus Ef, and guides the signal light having passed through the fundus Ef to the OCT unit 100.

An observation light source 11 of the illumination optical system 10 includes, for example, a halogen lamp. The light (observation illumination light) output from the observation light source 11 is reflected by a reflection mirror 12 having a curved reflective surface, and becomes near-infrared light after passing through a visible cut filter 14 via a condenser lens 13. Further, the observation illumination light is once converged near an imaging light source 15, reflected by a mirror 16, and passes through relay lenses 17 and 18, a diaphragm 19, and a relay lens 20. Then, the observation illumination light is reflected on the peripheral part (the surrounding region of an aperture part) of an aperture mirror 21, penetrates a dichroic mirror 46, and refracted by an objective lens 22, thereby illuminating the fundus Ef. Note that a light emitting diode (LED) may be used as the observation light source.

The observation illumination light reflected from the fundus is refracted by the objective lens 22, penetrates the dichroic mirror 46, passes through the aperture part formed in the center region of the aperture mirror 21, passes through a dichroic mirror 55, travels through a focusing lens 31, and is reflected by a mirror 32. Further, the fundus reflection light passes through a half mirror 33A, is reflected by a dichroic mirror 33, and forms an image on the light receiving surface of the CCD image sensor 35 by a condenser lens 34. The CCD image sensor 35 detects, for example, the fundus reflection light at a predetermined frame rate. An image (observation image) based on the fundus reflection light detected by the CCD image sensor 35 is displayed on a display device 3. Note that when the imaging optical system 30 is focused on the anterior eye segment, an observation image of the anterior eye segment of the subject's eye E is displayed.

The imaging light source 15 is formed of, for example, a xenon lamp. The light (imaging illumination light) output from the imaging light source 15 is irradiated to the fundus Ef via the same route as that of the observation illumination light. The imaging illumination light reflected from the fundus is guided to the dichroic mirror 33 via the same route as that of the observation illumination light, passes through the dichroic mirror 33, is reflected by a mirror 36, and forms an image on the light receiving surface of the CCD image sensor 38 by a condenser lens 37. The display device 3 displays an image (photographed image) based on the fundus reflection light detected by the CCD image sensor 38. Note that the same device or different devices may be used as the display device 3 for displaying an observation image and the display device 3 for displaying a photographed image. Besides, when similar photographing is performed by illuminating the subject's eye E with infrared light, an infrared photographed image is displayed. An LED may be used as the imaging light source.

A liquid crystal display (LCD) 39 displays a fixation target or a visual target for measuring visual acuity. The fixation target is a target for fixating the subject's eye E, and is used on the occasion of photographing of the fundus or OCT measurement.

Part of the light output from the LCD 39 is reflected by the half mirror 33A, reflected by the mirror 32, travels through the focusing lens 31 and the dichroic mirror 55, passes through the aperture part of the aperture mirror 21, penetrates the dichroic mirror 46, and is refracted by the objective lens 22, thereby being projected onto the fundus Ef.

By changing the display position of the fixation target on the screen of the LCD 39, the fixation position of the subject's eye E can be changed. Examples of the fixation position of the subject's eye E include, as with conventional fundus cameras, a position for acquiring an image centered on the macula of the fundus Ef, a position for acquiring an image centered on the optic papilla, a position for acquiring an image centered on the fundus center between the macula and the optic papilla, and the like. Further, the display position of the fixation target may be arbitrarily changed.

Further, as with conventional fundus cameras, the fundus camera unit 2 is provided with an alignment optical system 50 and a focus optical system 60. The alignment optical system 50 generates a target (alignment indicator) for the registration (alignment) of the optical system with respect to the subject's eye E. The focus optical system 60 generates a target (split target) for adjusting the focus with respect to the subject's eye E.

The light (alignment light) output from an LED 51 of the alignment optical system 50 travels through diaphragms 52 and 53 and a relay lens 54, is reflected by the dichroic mirror 55, passes through the aperture part of the aperture mirror 21, penetrates the dichroic mirror 46, and is projected onto the cornea of the subject's eye E by the objective lens 22.

The alignment light reflected from the cornea travels through the objective lens 22, the dichroic mirror 46 and the abovementioned aperture part. Part of the cornea reflection light penetrates the dichroic mirror 55, passes through the focusing lens 31, is reflected by the mirror 32, penetrates the half mirror 33A, is reflected by the dichroic mirror 33, and is projected onto the light receiving surface of the CCD image sensor 35 by the condenser lens 34. The display device 3 displays an image (alignment indicator) captured by the CCD image sensor 35 together with the observation image. A user conducts alignment by the same operation as performed on a conventional fundus camera. Instead, alignment may be performed in such a way that the arithmetic and control unit 200 analyzes the position of the alignment indicator and moves the optical system (automatic alignment).

To conduct focus adjustment, the reflective surface of a reflection rod 67 is arranged in a slanted position on the optical path of the illumination optical system 10. The light (focus light) output from an LED 61 of the focus optical system 60 passes through a relay lens 62, is split into two light beams by a split target plate 63, passes through a two-hole diaphragm 64, is reflected by a mirror 65, and is reflected after an image is once formed on the reflective surface of the reflection rod 67 by a condenser lens 66. Further, the focus light travels through the relay lens 20, is reflected by the aperture mirror 21, penetrates the dichroic mirror 46, and is refracted by the objective lens 22, thereby being projected onto the fundus Ef.

The focus light reflected from the fundus passes through the same route as the alignment light reflected from the cornea and is detected by the CCD image sensor 35. The display device 3 displays an image (split target) captured by the CCD image sensor 35 together with an observation image. As in the conventional case, the arithmetic and control unit 200 analyzes the position of the split target, and moves the focusing lens 31 and the focus optical system 60 for focusing (automatic focusing). The user may perform the focusing manually while visually checking the split target.

The dichroic mirror 46 branches an optical path for OCT measurement from an optical path for fundus photography. The dichroic mirror 46 reflects light of wavelengths used in OCT measurement, and transmits light for fundus photography. This optical path for OCT measurement is provided with, in order from the OCT unit 100 side, a collimator lens unit 40, an optical path length changing unit 41, a galvanometer scanner 42, a focusing lens 43, a mirror 44, and a relay lens 45.

The optical path length changing unit 41 is movable in directions indicated by the arrow in FIG. 1, thereby changing the length of the optical path for OCT measurement. This change in the optical path length is used for correcting the optical path length according to the axial length of the subject's eye E, adjusting the interference state, and the like. The optical path length changing unit 41 includes, for example, a corner cube and a mechanism for moving it.

The galvanometer scanner 42 changes the travelling direction of light (signal light LS) travelling through the optical path for OCT measurement. Thereby, the fundus Ef can be scanned with the signal light LS. The galvanometer scanner 42 includes, for example, a galvanometer mirror for scanning the signal light LS in the x direction, a galvanometer mirror for scanning the light in the y direction, and a mechanism for driving them independently. Accordingly, the signal light LS can be scanned in any direction on the xy plane.

[OCT Unit]

A description is given of an example of the configuration of the OCT unit 100 with reference to FIG. 2. The OCT unit 100 is provided with an optical system for acquiring an OCT image of the fundus Ef (OCT information). The optical system has a similar configuration to that of a conventional spectral-domain OCT device. That is, the optical system is configured to split low-coherence light into reference light and signal light, make the signal light having passed through the fundus Ef and the reference light having travelled through a reference optical path interfere with each other to generate interference light, and detect the spectral component of the interference light. The detection result (detection signal) is sent to the arithmetic and control unit 200.

Note that, in the case of swept-source OCT, a wavelength sweeping light source is provided instead of a light source that outputs low-coherence light, while an optical member for spectrally decomposing interference light is not provided. Generally, regarding the configuration of the OCT unit 100, known technologies may be applied according to the type of OCT.

A light source unit 101 outputs broadband, low-coherence light L0. The low-coherence light L0 has, for example, near-infrared wavelengths (approximately 800 nm to 900 nm), and a temporal coherence length of around several tens of micrometers. Note that, wavelengths not visible to the human eye, such as, for example, near-infrared light with a central wavelength of around 1040 nm to 1060 nm may be used as the low-coherence light L0.

The light source unit 101 includes a light output device, such as a super luminescent diode (SLD), an LED, a semiconductor optical amplifier (SOA), or the like.

The low coherence light L0 output from the light source unit 101 is guided to a fiber coupler 103 through an optical fiber 102 and split into signal light LS and reference light LR.

The reference light LR is guided through an optical fiber 104 and arrives at an optical attenuator 105. The optical attenuator 105 automatically adjusts the amount of the reference light LR guided through the optical fiber 104 under the control of the arithmetic and control unit 200 using a known technology. The reference light LR in the light amount having adjusted by the optical attenuator 105 is guided through the optical fiber 104 and arrives at a polarization adjuster (polarization controller) 106. The polarization adjuster 106 is a device that applies external stress to the looped optical fiber 104 to thereby adjust the polarization condition of the reference light LR guided through the optical fiber 104. Note that the configuration of the polarization adjuster 106 is not limited to this and any known technologies may be used. The reference light LR with polarization condition adjusted by the polarization adjuster 106 arrives at a fiber coupler 109.

The signal light LS generated by the fiber coupler 103 is guided through an optical fiber 107 and collimated into a parallel light beam by the collimator lens unit 40. Further, the signal light LS arrives at the dichroic mirror 46 via the optical path length changing unit 41, the galvanometer scanner 42, the focusing lens 43, the mirror 44, and the relay lens 45. Subsequently, the signal light LS is reflected by the dichroic mirror 46, refracted by the objective lens 22, and thereby projected onto the fundus Ef. The signal light LS is scattered (and/or reflected) at various depth positions of the fundus Ef. Back-scattered light of the signal light LS from the fundus Ef reversely advances along the same path as the outward path and is guided to the fiber coupler 103, thereby arriving at the fiber coupler 109 through an optical fiber 108.

The fiber coupler 109 causes the back-scattered light of the signal light LS and the reference light LR having passed through the optical fiber 104 to interfere with each other. Interference light LC thus generated is guided through an optical fiber 110 and output from an exit end 111. Further, the interference light LC is collimated into a parallel light beam by a collimator lens 112, spectrally divided (spectrally decomposed) by a diffraction grating 113, converged by a convergence lens 114, and projected onto the light receiving surface of a CCD image sensor 115. Note that although FIG. 2 illustrates the diffraction grating 113 of the transmission type, it is possible to use a spectrally decomposing element of any other type, such as a diffraction grating of reflection type.

The CCD image sensor 115 is, for example, a line sensor, and detects the spectral components of the spectrally decomposed interference light LC and converts the components into electric charges. The CCD image sensor 115 accumulates the electric charges to generate a detection signal, and sends the signal to the arithmetic and control unit 200.

Although a Michelson interferometer is employed in this embodiment, it is possible to employ any type of interferometer such as Mach-Zehnder-type as appropriate. Instead of the CCD image sensor, another type of image sensor, such as a complementary metal-oxide semiconductor (CMOS) image sensor, can be used.

[Arithmetic Controller]

Described blow is the configuration of the arithmetic and control unit 200. The arithmetic and control unit 200 analyzes a detection signal fed from the CCD image sensor 115 to form an OCT image of the fundus Ef. An arithmetic process for this is the same as that of a conventional spectral-domain OCT device.

The arithmetic and control unit 200 controls the fundus camera unit 2, the display device 3, and the OCT unit 100. For example, the arithmetic and control unit 200 displays an OCT image (OCT information) of the fundus Ef on the display device 3.

Further, for controlling the fundus camera unit 2, the arithmetic and control unit 200 controls the operation of the observation light source 11, the imaging light source 15 and the LEDs 51 and 61, the operation of the LCD 39, the movement of the focusing lenses 31 and 43, the movement of the reflection rod 67, the movement of the focus optical system 60, the movement of the optical path length changing unit 41, the operation of the galvanometer scanner 42, and the like.

For controlling the OCT unit 100, the arithmetic and control unit 200 controls the operation of the light source unit 101, the operation of the optical attenuator 105, the operation of the polarization adjuster 106, the operation of the CCD image sensor 115.

The arithmetic and control unit 200 is, for example, as in the conventional computer, a microprocessor, a random access memory (RAM), a read only memory (ROM), a hard disk drive, including a communication interface. The storage device such as a hard disk drive, a computer program for controlling the fundus observation apparatus 1 is stored. The arithmetic and control unit 200, various circuit boards, for example, may comprise a circuit board for forming an OCT image. Further, the arithmetic and control unit 200, an operation device (input device) such as a keyboard and a mouse, and may include a display device such as LCD.

The fundus camera unit 2, the display device 3, the OCT unit 100, and the arithmetic and control unit 200 may be integrally provided (i.e., in a single housing), or they may be separately provided in two or more housings.

[Control System]

Figure 3:
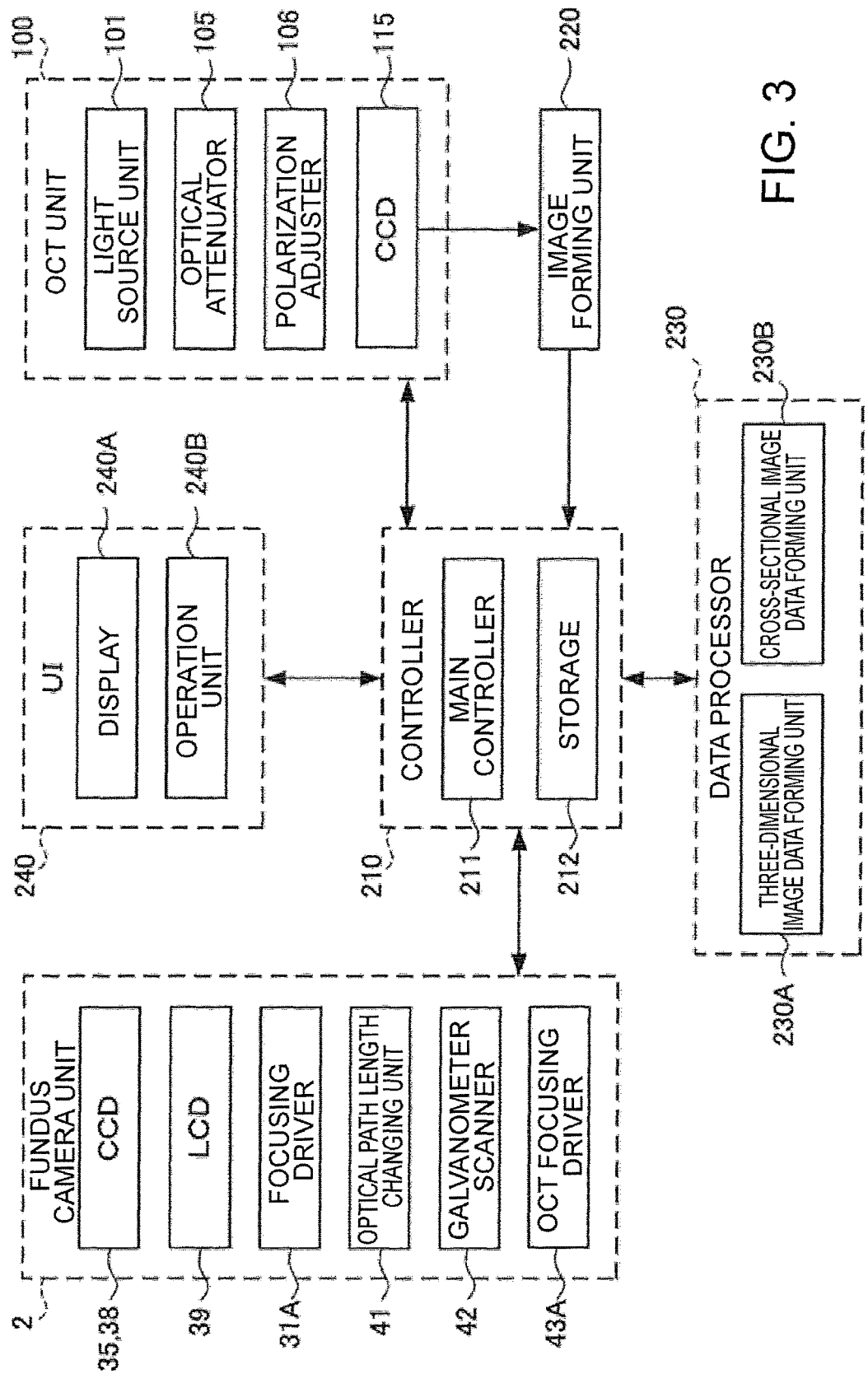
FIG. 3 is a schematic diagram illustrating an example of the configuration of the fundus observation apparatus of the embodiment.
Figure 4:
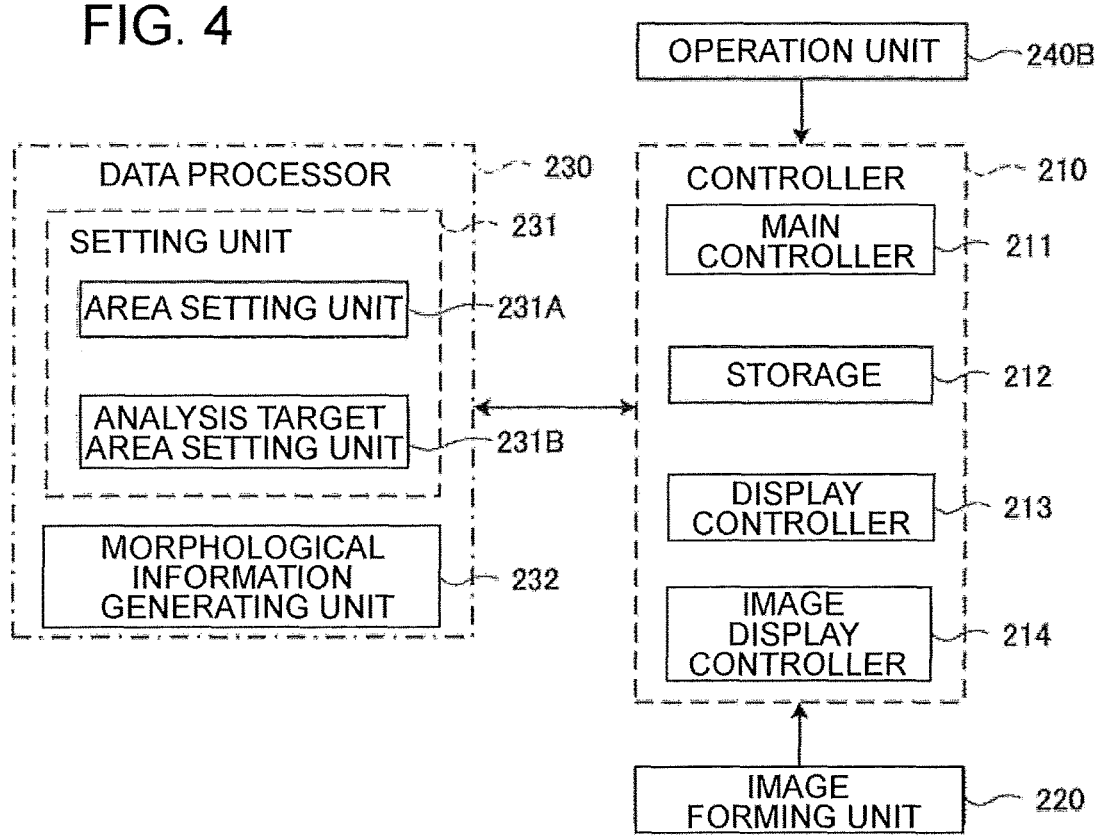
FIG. 4 is a schematic diagram illustrating an example of the configuration of the fundus observation apparatus of the embodiment.
Figure 5:
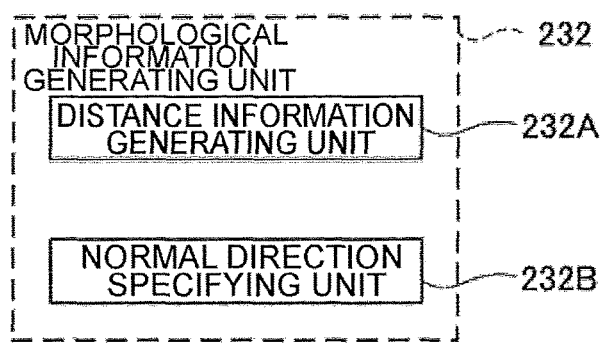
FIG. 5 is a schematic diagram illustrating an example of the configuration of the fundus observation apparatus of the embodiment.

The configuration of the control system of the fundus observation apparatus 1 is described with reference to FIGS. 3 to 5.

(Controller)

The control system of the fundus observation apparatus 1 is centered around a controller 210. The controller 210 includes, for example, the microprocessor, RAM, ROM, a hard disk drive, and a communication interface. The controller 210 is provided with a main controller 211, a storage 212, a display controller 213, and an image display controller 214.

(Main Controller)

The main controller 211 performs various types of controls mentioned above. In particular, the main controller 211 controls a focusing driver 31A of the fundus camera unit 2, the optical path length changing unit 41, the galvanometer scanner 42 and an OCT focusing driver 43A, the light source unit 101 of the OCT unit, the optical attenuator 105, and the polarization adjuster 106. In addition, the main controller 211 performs various display control described later.

The focusing driver 31A moves the focusing lens 31 in the optical axis direction. This changes the focus position of the imaging optical system 30. Incidentally, the main controller 211 may control an optical system driver (not illustrated) to three-dimensionally moves the optical system of the fundus camera unit 2. This control is used in alignment and tracking. Here, tracking is to move the optical system of the apparatus according to the eye movement of the subject's eye E. To perform tracking, alignment and focusing are performed in advance. Tracking is a function of causing the position of the optical system of the apparatus to follow the eye movement, thereby maintaining a suitable positional relationship in which alignment and focusing are adjusted.

The OCT focusing driver 43A moves the focusing lens 43 in the optical axis direction of the signal optical path. This changes the focus position of the signal light LS. The focus position of the signal light LS corresponds to the depth position (z position) of the beam waist of the signal light LS.

Further, the main controller 211 performs a process of writing data to the storage 212, and a process of reading out data from the storage 212.

(Storage)

The storage 212 stores various types of data. Examples of the data stored in the storage 212 include, for example, image data of an OCT image (OCT information), image data of a fundus image, and subject's eye information. The subject's eye information includes information related to a subject such as patient ID and name, information related to the subject's eye such as identification information of left eye/right eye, and the like. The storage 212 further stores various types of programs and data to run the fundus observation apparatus 1.

(Display Controller)

The display controller 213 displays various types of information generated by the controller 210 or a data processor 230 on a display 240A. Examples of the information generated by the controller 210 include operating conditions controlled by the main controller 211, information stored in the storage 212, and the like. Examples of information generated by the data processor 230 include morphological information indicating the morphology of a predetermined portion (e.g. the lamina cribrosa) of the fundus, and the like. The morphological information is described later.

(Image Display Controller)

The image display controller 214 displays images captured by applying OCT to the subject's eye on the display 240A. Examples of the images obtained by applying OCT include an OCT image that indicates the morphology of a predetermined portion of the fundus (described later), and the like. The functions of the image display controller 214 may be implemented by the display controller 213.

(Image Forming Unit)

An image forming unit 220 forms image data of a tomographic image of the fundus Ef based on a detection signal from the CCD image sensor 115. As in conventional spectral-domain OCT, this process includes noise removal (noise reduction), filtering, fast Fourier transform (FFT), and the like. In the case of another type of OCT device, the image forming unit 220 performs known processes according to the type thereof.

The image forming unit 220 includes, for example, the aforementioned circuit boards. Incidentally, "image data" and the "image" based thereon may be treated in the same way in this specification.

(Data Processor)

The data processor 230 performs various types of image processing and analysis on images formed by the image forming unit 220. For example, the data processor 230 performs various correction processes such as brightness correction and dispersion correction of the images. The data processor 230 performs various types of image processing and analysis on images (fundus image, anterior segment image, etc.) captured by the fundus camera unit 2. The data processor 230 may perform the above processing on an OCT image stored in the storage 212.

The data processor 230 includes a three-dimensional image data forming unit 230A and a cross-sectional image data forming unit 230B. The three-dimensional image data forming unit 230A performs known image processing such as an interpolation process for interpolating pixels in a plurality of tomographic images obtained along a plurality of scan lines, thereby forming three-dimensional image data of the fundus Ef. The three-dimensional image data refers to image data in which the positions of pixels are defined by a three-dimensional coordinate system. Examples of the three-dimensional image data include image data composed of three-dimensional arrays of voxels. This image data is referred to as volume data, voxel data, or the like.

For displaying an image based on the volume data, the data processor 230 performs a rendering process (e.g., volume rendering, MPR, maximum intensity projection (MIP), etc.) on the volume data to form image data of a pseudo three-dimensional image taken from a specific view direction. The pseudo three-dimensional image is displayed on the display 240A.

Further, stack data of a plurality of a plurality of tomographic images may be formed as the image data of a three-dimensional image. The stack data is image data obtained by three-dimensionally arranging tomographic images obtained along a plurality of scan lines based on the positional relationship of the scan lines. That is, the stack data is image data obtained by expressing the tomographic images, which are originally defined by their respective two-dimensional coordinate systems, by a three-dimensional coordinate system (i.e., embedding the images in a single three-dimensional space).

The cross-sectional image data forming unit 230B forms cross-sectional image data based on the three-dimensional image data formed by the three-dimensional image data forming unit 230A. This process is performed by, for example, performing MPR or the like on the three-dimensional image data. In the case of forming cross-sectional image data from the three-dimensional image data, the cross section is set manually or automatically.

The data processor 230 can perform registration between a fundus image and an OCT image. When a fundus image and an OCT image are obtained in parallel, the fundus image and the OCT image, which have been (almost) simultaneously obtained, can be registered with reference to the optical axis of the imaging optical system 30 since these optical systems are coaxial. Besides, regardless of the timing of obtaining the fundus image and the OCT image, registration between the fundus image and the OCT image can be achieved by registering the fundus image with an image obtained by projecting the OCT image onto the xy plane.

In this embodiment, the data processor 230 includes a setting unit 231 and a morphological information generating unit 232.

(Setting Unit)

The setting unit 231 includes an area setting unit 231A and an analysis target area setting unit 231B. The area setting unit 231A sets a front area corresponding to the front surface of the lamina cribrosa and a rear area corresponding to the rear surface of the lamina cribrosa. The front area and the rear area are in an OCT image (OCT information) stored in the storage 212. The lamina cribrosa includes at least an area in which a plurality of holes is formed to allow the optic nerves in the optic disc to pass therethrough. The front area is an area (layer area) corresponding to the boundary surface of the lamina cribrosa on the vitreous body side. The rear area is an area (layer area) corresponding to the boundary surface of the lamina cribrosa on the occipital side (i.e., on the opposite side to the vitreous body side of the lamina cribrosa). The lamina cribrosa area is located between the front area and the rear area in a direction from the vitreous body side toward the occipital side in the vicinity of the recessed portion of the optic disc.

In response to operation information based on user's operation on the operation unit 240B, the area setting unit 231A can set at least one of the front area and the rear area based on the operation information. Specifically, the image display controller 214 displays an OCT image on the display 240A. With respect to the image displayed on the display 240A, the area setting unit 231A sets at least one of the front area and the rear area based on a position that the user has specified using the operation unit 240B.

The area setting unit 231A may be configured to set at least one of the front area and the rear area of the lamina cribrosa by analyzing the OCT image. For example, the area setting unit 231A specifies a plurality of layer areas based on the pixel values (brightness values) of the OCT image. That is, the area setting unit 231A performs segmentation. The area setting unit 231A may be configured to select a predetermined layer area based on the pixel values and the shape of the OCT image. The area setting unit 231A may be configured to specify a characteristic site of the fundus Ef (e.g., a recessed portion, etc.) by analyzing the OCT image, and specify a predetermined layer area based on the relative positions with respect to the characteristic site. From among the layer area specified, the area setting unit 231A specifies, as a lamina cribrosa area, a layer area that includes an area corresponding to the holes of the lamina cribrosa. In general, a predetermined layer area can be specified by any known technique (image processing technique).

The area setting unit 231A may be configured to directly detect the holes of the lamina cribrosa based on the pixel values of the OCT image to specify an area having the holes of the lamina cribrosa detected as the lamina cribrosa area. Further, the area setting unit 231A may be configured to specify an area, in which collagen fiber that constitutes the lamina cribrosa is present, as the lamina cribrosa area. The area, in which collagen fiber is present, can be specified from a shadowgram obtained by composing a plurality of OCT images in the extending direction of the holes, for example.

The area setting unit 231A may also be configured to set the side area of the lamina cribrosa. The side area of the lamina cribrosa is an area located between the front area and the rear area. The area setting unit 231A may also set the side area manually or automatically.

In the case of manually setting the side area, based on a position that the user has specified using the operation unit 240B, the area setting unit 231A can set the side area of the lamina cribrosa with respect to an image displayed on the display 240A. When the front area and rear area of the lamina cribrosa are set manually or automatically as described above, and further when the user specifies an arbitrary position in the front area and an arbitrary position in the rear area using the operation unit 240B, the area setting unit 231A can connect between the two positions with a straight line or a predetermined curve to specify the boundary of the side area of the lamina cribrosa, thereby being able to set the side area of the lamina cribrosa.

In the case of automatically setting the side area, the area setting unit 231A can set the side area of the lamina cribrosa by analyzing an OCT image. For example, the area setting unit 231A follows the boundary of each of the front and rear areas of the lamina cribrosa, which have been set manually or automatically as described above, to specify the boundary of the side area, and set an area having the boundary as the side area. Further, for example, the area setting unit 231A specifies the endpoint of each of the front and rear areas of the lamina cribrosa, which have been set manually or automatically as described above, and sets, as the side area, an area specified by connecting between the two endpoints with a straight line or a predetermined curve.

Alternatively, the area setting unit 231A may set the side area of the lamina cribrosa by known region growing with reference to an arbitrary initial position in an OCT image. For example, the area setting unit 231A may be configured to set the side area by region growing in which an arbitrary position between the front and rear areas is set as an initial position and processing advances from the inside of the lamina cribrosa toward the outside. Examples of the arbitrary position between the front and rear areas include a position on a line segment connecting the center of the front area and the center of the rear area, a position on a line segment connecting the center of the gravity of the front area and the center of the gravity of the rear area, and the like. Besides, for example, the area setting unit 231A may specify the side area by region growing, in which a position that is away from each of the front and rear areas in at least the horizontal direction (xy direction) is set as an initial position and processing advances from the outside of the lamina cribrosa toward the inside. The region growing may include a process of searching for at least one of collagen fibers and holes of the lamina cribrosa.

The analysis target area setting unit 231B sets an area in an OCT image that includes at least the front and rear areas as an analysis target area. The analysis target area setting unit 231B may be configured to set an area in an OCT image including the side area of the lamina cribrosa as an analysis target area. Examples of the analysis target area include an area which is less susceptible to the influence of the blood vessels and where the lamina cribrosa is clearly rendered, an area where highly reliable results can be achieved from OCT measurement, and the like. Based on the analysis target area set by the analysis target area setting unit 231B, the morphological information generating unit 232 generates morphological information indicating the morphology of the lamina cribrosa. With this, the morphological information generating unit 232 can generate reliable information about the morphology of the lamina cribrosa.

In response to operation information based on user's operation on the operation unit 240B, the analysis target area setting unit 231B can set the analysis target area based on the operation information. Specifically, the image display controller 214 displays an OCT image on the display 240A. The analysis target area setting unit 231B sets the analysis target area for the image displayed on the display 240A based on the position specified through the operation unit 240B.

Further, the analysis target area setting unit 231B can set the analysis target area by analyzing the OCT image. The analysis target area setting unit 231B specifies the analysis target area based on, for example, the pixel values of the OCT image. In this case, the analysis target area setting unit 231B specifies the analysis center in the front area or the rear area set by the area setting unit 231A based on the pixel values of the OCT image. The analysis target area setting unit 231B may specify a characteristic part of the fundus Ef (the optic disc, an area having characteristic pixel values, etc.) as the analysis center. The analysis center may be a predetermined area in the fundus Ef or a predetermined layer area in a tomographic image of the fundus Ef. Examples of the predetermined area in the fundus Ef include (the center of) the optic disc and the like. Examples of the predetermined layer area in the tomographic image of the fundus Ef include Bruch's membrane opening (BMO) and the like. In addition, the analysis center may be the center of the gravity of the optic disc. When the analysis center is specified, the analysis target area setting unit 231B specifies a range within a predetermined distance from the analysis center as the analysis target area.

The analysis target area setting unit 231B may divide the OCT image into a plurality of grids, and set the analysis target area in unit of sector formed of a combination of one or more grids. For example, the divisional grids can be obtained by dividing the area radially from the analysis center, by dividing the area with one or more concentric circles around the analysis center, dividing the area into a grid pattern, and the like.

In addition, the analysis target area setting unit 231B may set the analysis target area to include only one of the front and rear areas.

(Morphological Information Generating Unit)

The morphological information generating unit 232 generates morphological information indicating the morphology of the lamina cribrosa based on at least the front area and the rear area. Besides, the morphological information generating unit 232 can generate morphological information indicating the morphology of the lamina cribrosa based on the side area. Examples of the morphological information include a parameter indicating: the inclination of the front area, the rear area, and/or the side area of the lamina cribrosa; the inclination of the lamina cribrosa; the distance between the front area and the rear area in a predetermined direction; the curvature of the front area and/or that of the rear area; the area of the side area; the distribution of the holes; and, the shape of the analysis target area and/or that of the lamina cribrosa area. Examples of the parameter indicating the distribution of the holes include: the number of the holes; thickness of the hole; area of the hole; extending state of the hole; the major axis and the minor axis of an approximate ellipse that approximates the hole; and, the inclination of the major axis and the minor axis. Examples of the parameter for the shape of the lamina cribrosa area and/or that of the analysis target area include the major axis and the minor axis of an approximate ellipse that approximates the area, and the inclination of the major axis and the minor axis, the area of the approximate ellipse, and the like. When the analysis target area is set by the analysis target area setting unit 231B, the morphological information generating unit 232 generates the morphological information based on the front area and the rear area in the analysis target area. Further, the morphological information generating unit 232 can generate morphological information based on the side area in the analysis target area.

The morphological information generating unit 232 includes a distance information generating unit 232A and a normal direction specifying unit 232B. The morphological information generating unit 232 can generate distance information indicating the distance between the front area and the rear area as the morphological information. The distance information generating unit 232A generates, as the morphological information, the distance information between the front area and the rear area of the lamina cribrosa set by the area setting unit 231A. More specifically, the distance information generating unit 232A generates distance information indicating a distance between the front area and the rear area in a predetermined measurement direction as the morphological information. In this embodiment, the measurement direction corresponds to the normal direction specified by the normal direction specifying unit 232B. The normal direction specifying unit 232B specifies the normal direction of the front area or the rear area of the lamina cribrosa. Thereby, the distance information generating unit 232A can generate the distance information as the morphological information based on the normal direction specified by the normal direction specifying unit 232B.

As the distance information between the front and rear areas (or the front and rear areas in the analysis target area), the distance information generating unit 232A can generate information on the distance between the areas, or a statistics or distribution of the distances between the two or more measurement points set in each of the areas. Examples of information indicating the distance between the areas include the distance between the center of the gravity of one area and that of the other, the distance from a measurement point of the front area or the rear area in the normal direction specified in the area, the distance between two points arbitrarily set in each of the areas, and the like. Examples of the statistics of the distances include the average, standard deviation, median, maximum value, and minimum value of values indicating two or more pieces of distance information between the front area and the rear area. The distance information generating unit 232A may obtain the distance between the front area and the rear area (or the front area and the rear area in the analysis target area) in the measurement direction passing through a measurement point set in advance.

The morphological information generating unit 232 can set the measurement point with respect to an OCT image in a predetermined arrangement pattern. The arrangement pattern defines a plurality of measurement points in a grid, concentric circles, or radially based on the reference position such as the center of the optic disc. The arrangement pattern may define a plurality of measurement points mainly near the macula, in the front area, or in the rear area. The arrangement pattern may be formed of a combination of at least two of the above examples. Further, part or all of the measurement points may be set manually.

The normal direction specifying unit 232B can obtain an approximate curved surface by applying a known curved surface approximation to the front area or the rear area, and specify the normal direction for each of measurement points in the approximate curved surface. The normal direction specifying unit 232B may obtain an approximate curved surface by applying a known curved surface approximation to the inner limiting membrane (ILM), the nerve fiber layer (NFL), the boundary of the Bruch's membrane opening (BMO), or the contour of the optic disc, and specify a normal direction from among those of the approximate curved surface, which passes through the measurement point.

Besides, the OCT image (OCT information) may include a two-dimensional data set or a three-dimensional data set. In this case, the morphological information generating unit 232 generates distribution information of a parameter that indicates the morphology of the lamina cribrosa as the morphological information based on the two-dimensional or three-dimensional data set. Examples of the parameter indicating the morphology of the lamina cribrosa include the distance determined for each intersection of the A-line and the front area or the rear area, and the like. The display controller 213 can display the distribution information on the display 240A according to the values of the parameter.

The data processor 230 that functions as above includes, for example, a microprocessor, RAM, ROM, a hard disk drive, a circuit board, and the like. The storage device such as a hard disk drive stores, in advance, computer programs for causing the microprocessor to implement the above functions.

(User Interface)

A user interface 240 includes the display 240A and the operation unit 240B. The display 240A includes the aforementioned display device of the arithmetic and control unit 200 and the display device 3. The operation unit 240B includes the aforementioned operation device of the arithmetic and control unit 200. The operation unit 240B may include various types of buttons and keys provided on the case of the fundus observation apparatus 1 or the outside. For example, if the fundus camera unit 2 has a case similar to that of the conventional fundus camera, the operation unit 240B may include a joy stick, an operation panel, and the like provided to the case. Besides, the display 240A may include various types of display devices, such as a touch panel, arranged on the case of the fundus camera unit 2.

Note that the display 240A and the operation unit 240B need not necessarily be formed as separate devices. For example, a device like a touch panel, which has a display function integrated with an operation function, can be used. In such cases, the operation unit 240B includes the touch panel and a computer program. The content of operation performed on the operation unit 240B is fed to the controller 210 in the morphology of an electrical signal. Moreover, operations and inputs of information may be performed by using a graphical user interface (GUI) displayed on the display 240A and the operation unit 240B.

The OCT unit 100 and the data processor 230 are an example of the "OCT information generating unit" of the embodiment. Incidentally, the OCT unit 100, the image forming unit 220, and the data processor 230 may be an example of the "OCT information generating unit" of the embodiment.

[Scanning of Signal Light and OCT Images]

Described below are the scanning of the signal light LS and an OCT image.

Examples of scan modes of the fundus observation apparatus 1 for scanning the signal light LS include horizontal scan, vertical scan, cross scan, radial scan, circle scan, concentric scan, helical (spiral) scan, and the like. The scan modes are selectively used as appropriate in consideration of the site of the fundus to be observed, an object to be analyzed (the morphology of the lamina cribrosa, etc.), time required for scanning, scanning accuracy, and the like.

In the horizontal scan mode, the signal light LS is scanned in the horizontal direction (x direction). The horizontal scan mode includes the scan of the signal light LS along a plurality of scan lines arranged in the vertical direction (y direction) and extending in the horizontal direction. In this mode, the interval between the scan lines can be arbitrarily set. Besides, the scan lines are adjacent to one another at sufficiently narrow intervals to form a three-dimensional image as described above (three-dimensional scan). The same applies to the vertical scan.

In the cross scan mode, the signal light LS is scanned along a cruciform trajectory consisting of two straight trajectories that are perpendicular to each other. In the radial scan mode, the signal light LS is scanned along radial trajectories including a plurality of straight trajectories arranged at a predetermined angle. The cross scan is an example of the radial scan.

In the circle scan mode, the signal light LS is scanned along a circular trajectory. In the concentric scan mode, the signal light LS is scanned along a plurality of circular trajectories arranged concentrically around a predetermined center position. The circle scan is an example of the concentric scan. In the helical scan mode, the signal light LS is scanned along a helical (spiral) trajectory while the rotation radius is gradually reduced (or increased).

The galvanometer scanner 42 is configured to scan the signal light LS in directions perpendicular to each other, and therefore, is capable of scanning the signal light LS in the x and y directions independently. Further, by controlling the orientations of two galvanometer mirrors in the galvanometer scanner 42 at the same time, the signal light LS can be scanned along an arbitrary trajectory on the xy plane. Thus, it is possible to implement a variety of scan modes as described above.

By scanning the signal light LS in the manner described above, it is possible to acquire a tomographic image in a plane spanned in a direction along the scan lines (scan trajectories) and the depth direction of the fundus (z direction). Besides, particularly when the scan lines are arranged at a narrow interval, the three-dimensional image as described above can be obtained.

An area on the fundus Ef to be scanned by the signal light LS as described above, i.e., an area on the fundus Ef subjected to OCT measurement, is referred to as "scan area". The scan area in a three-dimensional scan is a rectangular area, in which a plurality of horizontal scan lines is arranged. The scan area in a concentric scan is a disc-shaped area surrounded by the trajectory of circle scan with the largest diameter. In addition, the scan area in a radial scan is a disc-shaped (or polygonal) area connecting the ends of the scan lines.

Operation Example

Described below is an example of the operation the fundus observation apparatus 1 of this embodiment.

Figure 6:
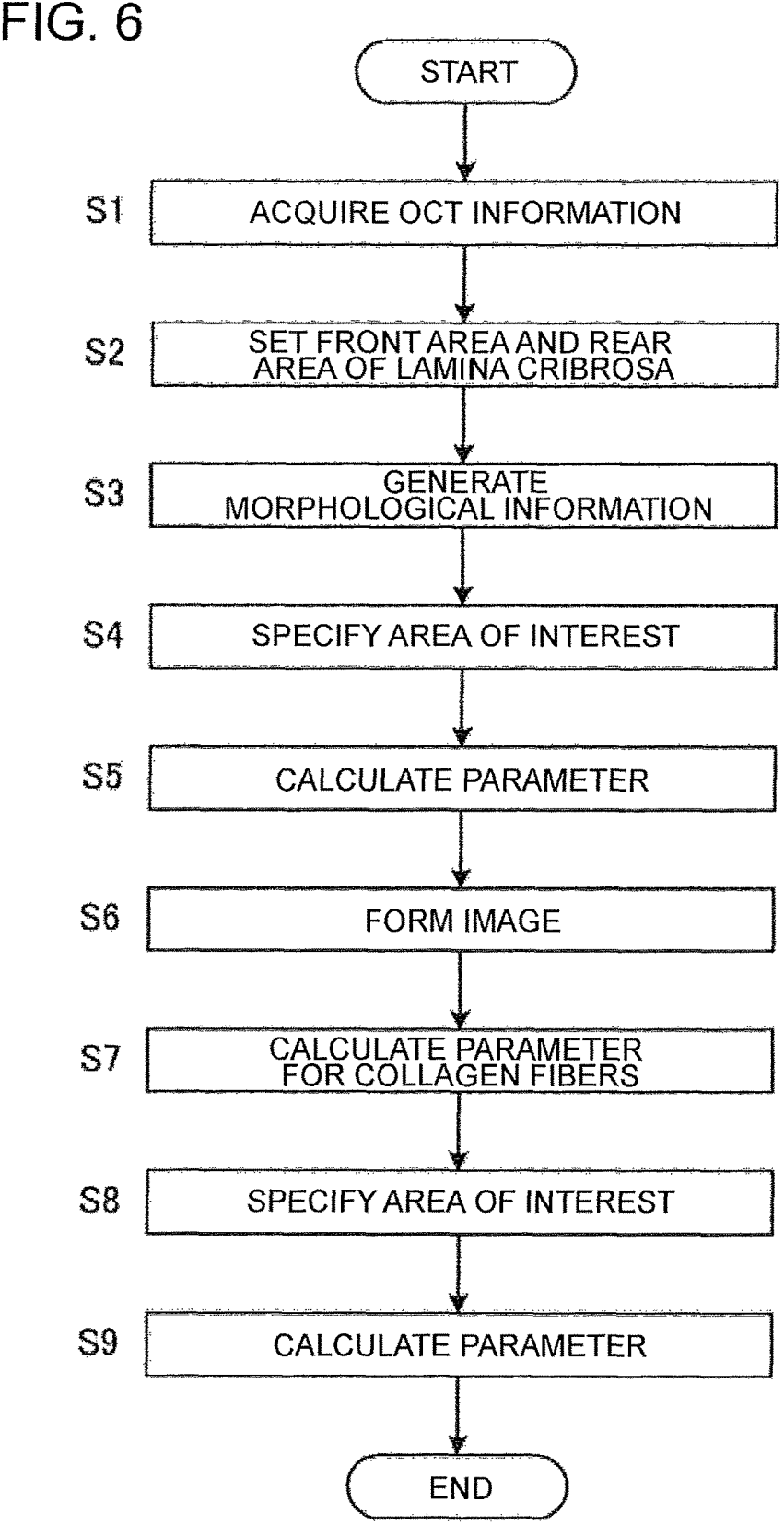
FIG. 6 is a flowchart illustrating an example of the operation of the fundus observation apparatus of the embodiment.
Figure 7:
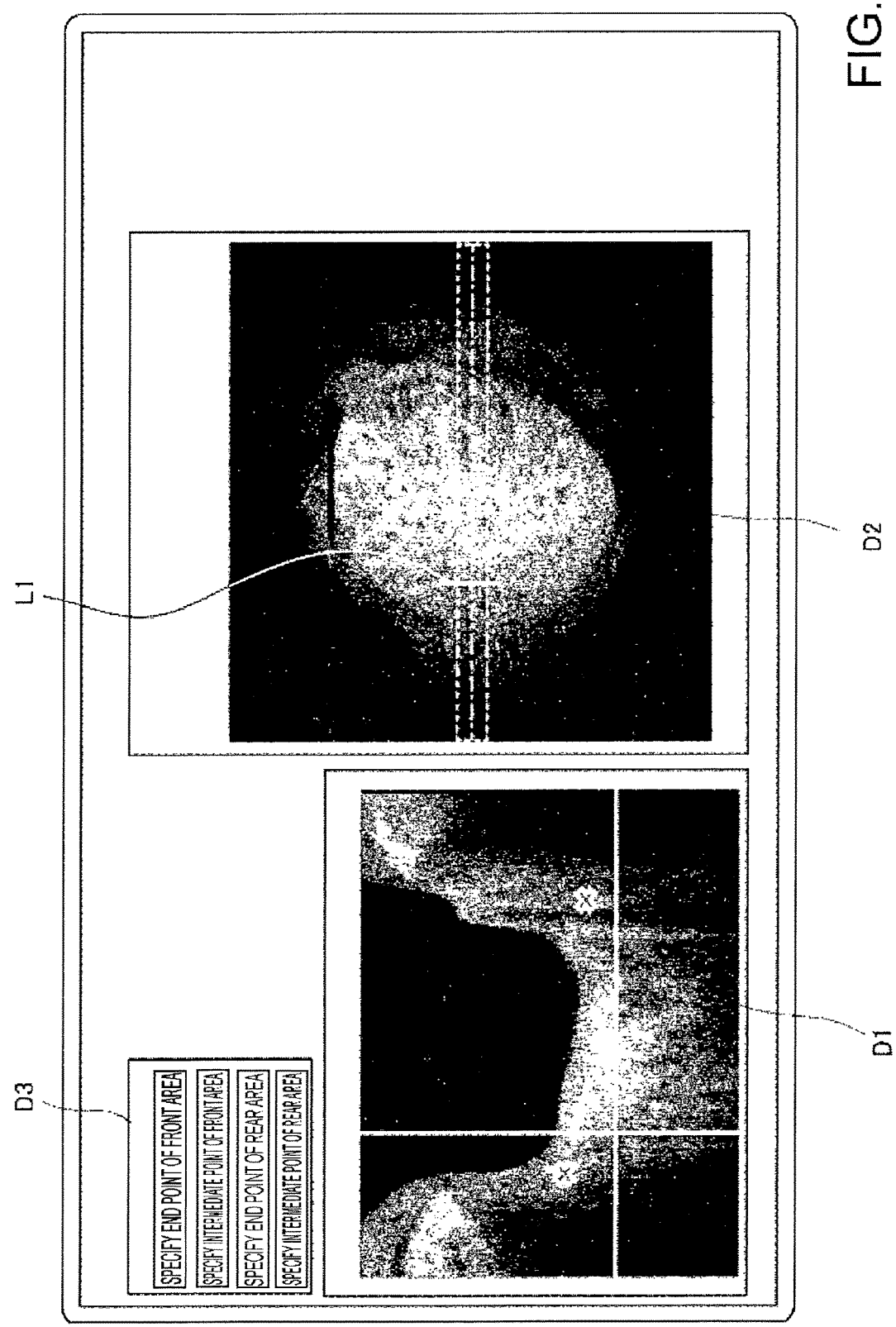
FIG. 7 is a diagram for explaining the operation of the fundus observation apparatus of the embodiment.
Figure 8:
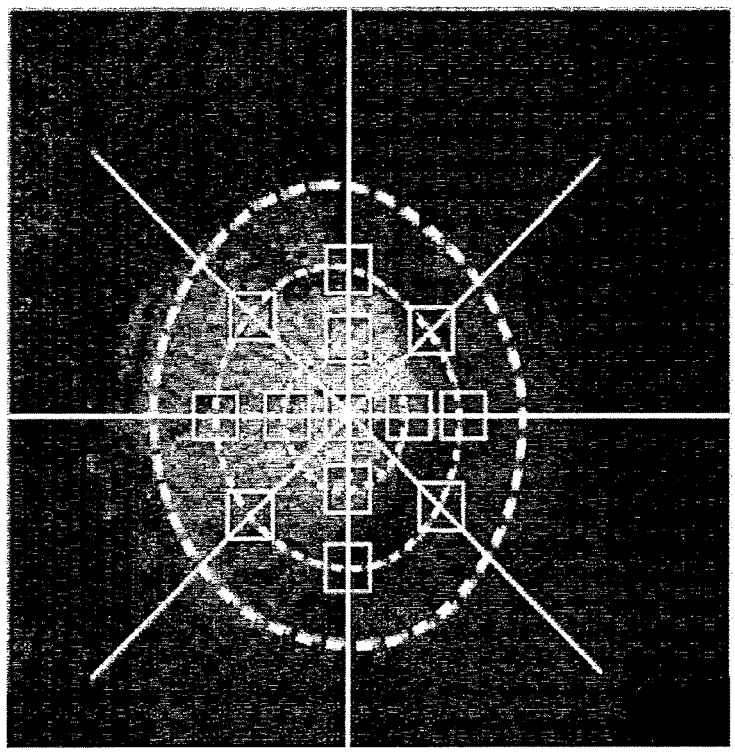
FIG. 8 is a diagram for explaining the operation of the fundus observation apparatus of the embodiment.
Figure 9:
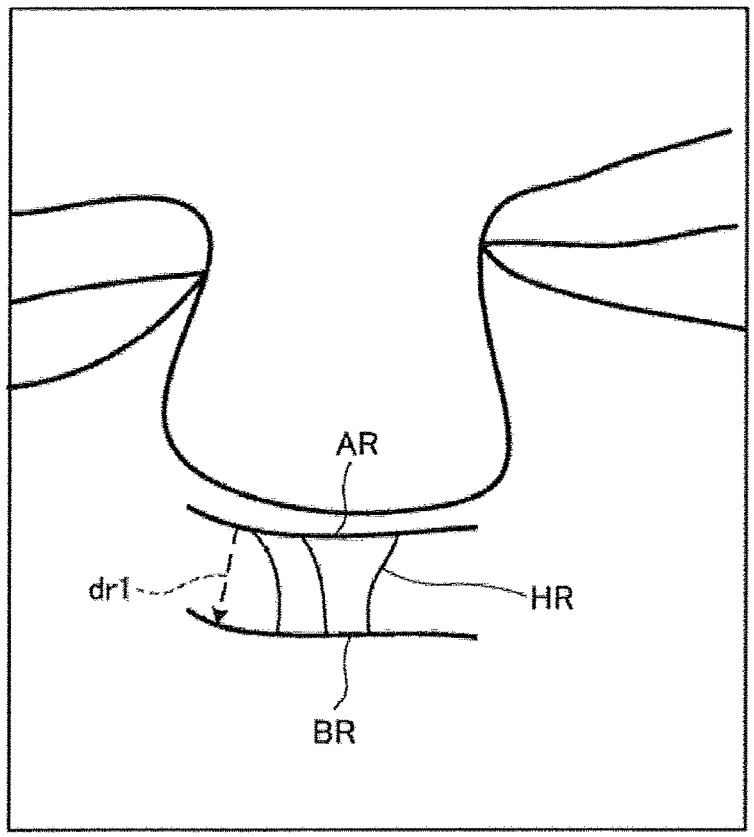
FIG. 9 is a diagram for explaining the operation of the fundus observation apparatus of the embodiment.

FIG. 6 is a flowchart illustrating an example of the operation of the fundus observation apparatus 1. It is assumed herein that alignment and focusing have been completed, and a fixation target is presented to the subject's eye E. FIGS. 7 to 9 are diagrams for explaining the operation of the fundus observation apparatus 1. FIG. 7 illustrates an example of an image displayed on the display 240A when the front and rear areas are set manually. FIG. 8 illustrates an example of a plurality of measurement points set by the morphological information generating unit 232. FIG. 9 schematically illustrates an example of a tomographic image of an area near the lamina cribrosa.

(S1)

First, in the state where the subject eye is fixated at a fixation position to acquire an image centered on the optic disc, the main controller 211 controls the light source unit 101, the galvanometer scanner 42, etc. to scan the area including the optic disc of the fundus Ef with the signal light LS. The image forming unit 220 forms one or more tomographic images according to the scan mode. The one or more tomographic images formed by the image forming unit 220 are stored in the storage 212 as OCT images (OCT information).

(S2)

Next, based on the one or more tomographic images acquired in step S1, the data processor 230 specifies the front area and the rear area of the lamina cribrosa. This process is performed by the area setting unit 231A. The area setting unit 231A specifies a plurality of layer areas based on the pixel values of the tomographic image acquired in step S1. Then, the area setting unit 231A specifies, as a lamina cribrosa area, a layer area including an area corresponding to the holes of the lamina cribrosa from among the layer areas specified.

When the rear and front areas are set manually, the main controller 211 performs a three-dimensional scan on that area, and the image forming unit 220 forms a front image based on the tomographic images acquired in step S1. As illustrated in FIG. 7 the image display controller 214 displays a B-scan image D1 and a C-scan image D2 side-by-side on the display 240A such that rendered position (sectional position) of the B-scan image can be identified in the C-scan image. In FIG. 7, the rendered position of the B-scan image D1 corresponds to a line L1 in the C-scan image D2. The area setting unit 231A sets the front and rear areas based on positions specified through the operation unit 240B with respect to the images displayed on the display 240A. The image display controller 214 displays the input mode setting part D3 above the B-scan image D1. The input mode setting part D3 is provided with mode specifying parts for specifying any of the end point of the front area, the intermediate point of the front area, the end point of the rear area, and the intermediate point of the rear area. By specifying a desired mode specifying part(s) with the operation unit 240B, the user can manually specify at least one of the end point of the front area, the intermediate point of the front area, the end point of the rear area, and the intermediate point of the rear area in the B-scan image D1 or the C-scan image D2. The front area and the rear area are connected by a straight line or a curve by specifying the end point and the intermediate point, and thus the areas are defined. Incidentally, the user can manually perform fine adjustment of the straight line or the curve that connects end points or intermediate points.

As described above, the area setting unit 231A can set the side area of the lamina cribrosa. The area setting unit 231A can also specify the side area manually or automatically.

(S3)

Next, based on the front and rear areas of the lamina cribrosa (or side area of the lamina cribrosa) specified in step S2, the data processor 230 generates morphological information indicating the morphology of the lamina cribrosa. For example, as illustrated in FIG. 8, the morphological information generating unit 232 sets a plurality of measurement points around the center of the optic disc, and generates information on the distance (distance information) between the front area and the rear area for each of the measurement points. FIG. 8 illustrates an example in which a plurality of measurement points (center points of a plurality of square images) are set on concentric circles at positions of ⅓ and ⅔ of the diameter of the optic disc in the circumferential direction on the basis of the center of the optic disc.

For example, as illustrated in FIG. 9, the normal direction specifying unit 232B applies curved surface approximation to the front area AR among the front area AR and the rear area BR, and specifies the normal direction at a measurement point in the approximate curved surface as a measurement direction dr1. In this embodiment, as illustrated in FIG. 9, the area where a hole portion HR of the lamina cribrosa is rendered corresponds to the lamina cribrosa area.

For example, the normal direction specifying unit 232B may obtain the normal direction of the front area for each A-line. Besides, the normal direction specifying unit 232B may apply curved surface approximation to the front area in a B-scan image, and specify the normal direction at the measurement point as the measurement direction. The normal direction specifying unit 232B may create a surface that approximates the front area in a three-dimensional area generated from a plurality of tomographic images acquired, and specify the normal direction at the measurement point in the surface created as the measurement direction.

In addition to or instead of the distance information, the morphological information generating unit 232 can generate, as the morphological information, information indicating the area of the front area, the lamina cribrosa area, or the rear area, the volume of the lamina cribrosa area, the curvature of the front area or the rear area, the inclination of the front area, the lamina cribrosa area, or the rear area, or the like.

(S4)

Next, the data processor 230 specifies an area of interest based on the morphological information generated in step S3. For example, the data processor 230 specifies an area including a characteristic position as the area of interest based on the morphological information. Examples of the characteristic position include a position where the value indicated by the morphological information is more than or less than a predetermined threshold, a position where the value indicated by the morphological information is within a predetermined range, a position where the amount of change in the values indicated by the morphological information is more than or less than a predetermined threshold, and the like.

(S5)

The data processor 230 calculates a parameter indicating the change in the area of interest specified in step S4. The parameter calculated by the data processor 230 is associated with position information indicating the position of the area of interest, the measurement point where the parameter has been calculated, or the vicinity thereof, and stored in the storage 212. By chronologically analyzing parameters calculated based on OCT images acquired at different timings for the same area of interest, trend analysis can be achieved. Besides, the parameter may be displayed in association with an event, such as dosing date, treatment date, examination date, or the like.

(S6)

Next, the image forming unit 220 forms an image that represents distribution information of the parameter that indicates the morphology of the lamina cribrosa generated by the morphological information generating unit 232. The distribution information may be distribution information of the parameter at a predetermined timing, or it may be distribution information indicating the amount of change in the parameter in time-series. The display controller 213 displays an image representing the distribution information on the display 240A.

The data processor 230 generates an approximate curved surface so as to include the measurement point set by the morphological information generating unit 232 or the vicinity thereof to create three-dimensional volume data. The image forming unit 220 generates a front image (C-scan image, projection image, shadowgram) based on the three-dimensional volume data. Further, the image forming unit 220 creates a front image after flattening based on the three-dimensional volume data such that the boundary of a predetermined layer area is to be flattened (to be the same z-coordinate value).
(S7)

The data processor 230 calculates parameter for the collagen fibers that form the holes of the lamina cribrosa and the lamina cribrosa using the front image created in step S6. Examples of the parameter of the collagen fibers include the thickness of collagen fiber, the area or volume of collagen fiber, the vector indicating the running of collagen fiber, and the like. The morphological information generating unit 232 detects an area corresponding to the holes of the lamina cribrosa based on the front image created in step S6, and calculates the size (major axis, minor axis, or inclination of the approximate ellipse), the area, the volume, and the travel vector of the holes.
(S8)

Next, as in step S4, the data processor 230 specifies an area of interest based on the morphological information and/or the parameter calculated in step S7. For example, the data processor 230 specifies an area including a characteristic position as the area of interest based on the parameter and/or the morphological information.
(S9)

As in step S5, the data processor 230 calculates a parameter indicating the change in the area of interest specified in step S8. The parameter calculated by the data processor 230 is associated with position information indicating the position of the area of interest, the measurement point where the parameter has been calculated, or the vicinity thereof, and stored in the storage 212. By chronologically analyzing the parameter calculated based on OCT images acquired at different timings for the same area of interest, trend analysis can be achieved. Besides, the parameter may be displayed in association with an event as in step S5.

Effects

A description is given of the arithmetic and control unit 200 of the embodiment and the fundus observation apparatus 1 including the arithmetic and control unit 200. A fundus analysis apparatus can be realized as a part of the fundus observation apparatus 1 as with the arithmetic and control unit 200. Besides, a fundus analysis apparatus may not have the function of OCT measurement and/or the function of fundus photography.

The arithmetic and control unit 200 (fundus analysis apparatus) includes the storage 212, the area setting unit 231A, and the morphological information generating unit 232. The storage 212 stores an OCT image (OCT information) acquired by applying OCT to the fundus Ef of the eye. The area setting unit 231A is configured to set a front area corresponding to the front surface of the lamina cribrosa and a rear area corresponding to the rear surface of the lamina cribrosa in the OCT image stored in the storage 212. The morphological information generating unit 232 is configured to generate morphological information indicating the morphology of the lamina cribrosa based on at least the front area and the rear area.

With the arithmetic and control unit 200, it is possible to acquire new information about the lamina cribrosa. By using the newly acquired information on the lamina cribrosa, it is possible to evaluate and diagnose glaucoma as well as to perform presymptomatic diagnosis more accurately.

The morphological information generating unit 232 may generate distance information indicating the distance between the front area and the rear area as the morphological information. With the arithmetic and control unit 200, the distance information that represents the distance between the front area and the rear area of the lamina cribrosa can be acquired as new information on the lamina cribrosa.

The arithmetic and control unit 200 may include the analysis target area setting unit 231B. The analysis target area setting unit 231B is configured to set an area including at least the front area and the rear area in the OCT image stored in the storage 212 as an analysis target area. The morphological information generating unit 232 may generate the morphological information based on the analysis target area set by the analysis target area setting unit 231B. In this manner, by arbitrarily setting the analysis target area, for example, an area which is less susceptible to the influence of the blood vessels and where the lamina cribrosa is clearly rendered, and thus where highly reliable results can be achieved from OCT measurement can be set as the analysis target area. In this case, the morphological information generating unit 232 can generate reliable information about the morphology of the lamina cribrosa.

The OCT image stored in the storage 212 may include a two-dimensional or three-dimensional data set. The morphological information generating unit 232 may generate distribution information of a parameter indicating the morphology of the lamina cribrosa as the morphological information based on the data set. The arithmetic and control unit 200 may further include the display controller 213. The display controller 213 is configured to display the distribution information generated by the morphological information generating unit 232 on the display 240A (display means) according to the values of the parameter. With the arithmetic and control unit 200, information is displayed on the display 240A such that the morphology of the lamina cribrosa can be recognized easily. Thus, it is possible to evaluate and diagnose the glaucoma as well as to perform presymptomatic diagnosis more accurately.

The arithmetic and control unit 200 may further include the image display controller 214, and have the function of the operation unit 240B. The image display controller 214 is configured to display an image based on the OCT image stored in the storage 212 on the display 240A. The area setting unit 231A is configured to set at least one of the front area and the rear area based on a position specified using the operation unit 240B with respect to the image displayed on the display. With the arithmetic and control unit 200, the user can set the front area and/or the rear area of the lamina cribrosa using the operation unit 240B while viewing the image displayed on the display 240A. This enables the analysis of the front area and/or the rear area desired by the user.

The fundus observation apparatus 1 may include an OCT information generating unit (the OCT unit 100 and the data processor 230) and the arithmetic and control unit 200. The OCT information generating unit is configured to generate an OCT image by applying OCT to the fundus Ef of the eye.

With the fundus observation apparatus 1, new information can be acquired regarding the lamina cribrosa.

First Modification

According to the above embodiment, the morphological information generating unit 232 specifies the normal direction of the front area of the lamina cribrosa or the like, and generates the morphological information using the specified normal direction as the measurement direction. However, embodiments are not so limited. The morphological information generating unit may be configured to generate the morphological information based on the distribution of the holes of the lamina cribrosa (e.g., the number, thickness, extending state of the holes, etc.). According to a first modification of the embodiment, the morphological information generating unit generates the morphological information based on the orientation of an image area corresponding to the holes of the lamina cribrosa.

The fundus observation apparatus of the first modification has basically a similar configuration to that of the fundus observation apparatus of the above embodiment. In the following, the fundus observation apparatus of the first modification is described focusing on the differences from that of the above embodiment.

Figure 10:
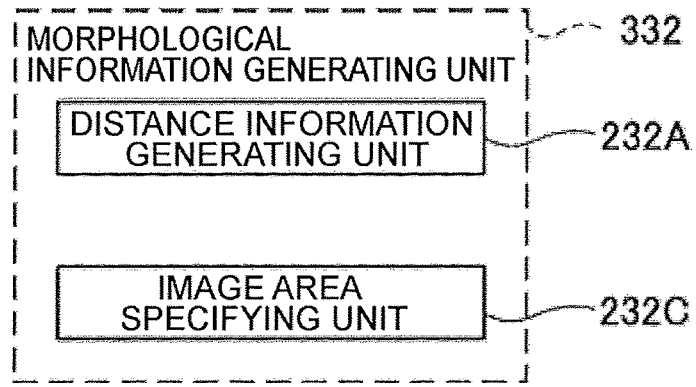
FIG. 10 is a schematic diagram illustrating an example of the configuration of a fundus observation apparatus according to a first modification of the embodiment.

FIG. 10 is a block diagram of an example of the configuration of a morphological information generating unit according to the first modification. In FIG. 10, like reference numerals designate like parts as in FIG. 5, and the same description may not be repeated. Instead of the morphological information generating unit 232 of the data processor 230 illustrated in FIG. 4, a morphological information generating unit 332 illustrated in FIG. 10 can be used.

The morphological information generating unit 332 includes the distance information generating unit 232A and an image area specifying unit 232C. The image area specifying unit 232C specifies an image area corresponding to the holes of the lamina cribrosa based on an OCT image stored in the storage 212. The morphological information generating unit 332 generates morphological information based on the orientation of the image area specified by the image area specifying unit 232C.

Figure 11:
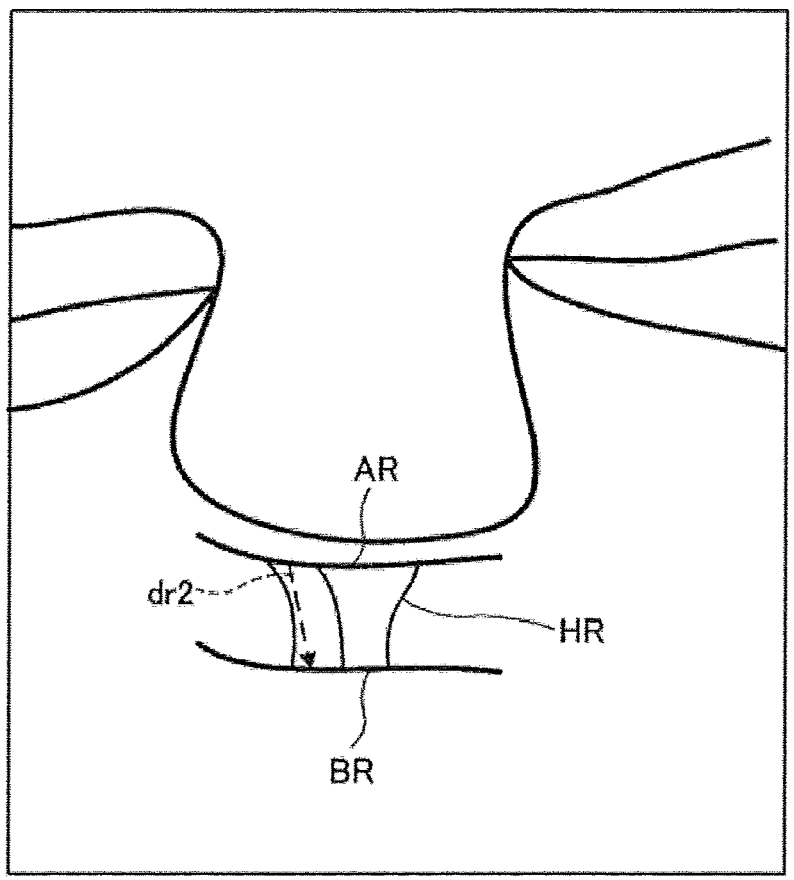
FIG. 11 is a diagram for explaining the operation of the fundus observation apparatus of the first modification of the embodiment.

From the pixel values of the tomographic image generated based on the OCT image, the image area specifying unit 232C specifies an image area corresponding to the holes of the lamina cribrosa and the orientation thereof as the extending direction of the holes of the lamina cribrosa. For example, as illustrated in FIG. 11, the image area specifying unit 232C specifies an image area corresponding to the hole portion HR of the lamina cribrosa in a B-scan image. The image area specifying unit 232C then approximates the extending direction of the hole portion HR by a straight line or a curve starting from the front area AR among the front area AR and the rear surface area BR to specify the measurement direction dr2. Besides, the image area specifying unit 232C may approximate the extending direction of the hole portion HR of the lamina cribrosa in the three-dimensional area generated from a plurality of tomographic images acquired, and specify the extending direction starting from a measurement point in the front area or the rear area as the measurement direction. Incidentally, when the direction of a line connecting the upper and lower ends of one of the holes is used as the measurement direction, the above approximation is not required.

As described above, according to the first modification, it is possible to obtain the morphological information indicating the morphology of the lamina cribrosa with respect to the extending direction of the hole portion of the lamina cribrosa. Thus, as in the above embodiment, it is possible to contribute to the evaluation and diagnosis of glaucoma as well as presymptomatic diagnosis and the like.

Second Modification

According to the first modification of the above embodiment, the morphological information generating unit 332 is configured to generate morphological information based on the orientation of the image area corresponding to the holes of the lamina cribrosa. However, the embodiment is not so limited. According to a second modification of the embodiment, the morphological information generating unit is configured to generate morphological information based on a direction set in advance.

The fundus observation apparatus of the second modification has basically a similar configuration to that of the fundus observation apparatus of the above embodiment. In the following, the fundus observation apparatus of the second modification is described focusing on the differences from that of the above embodiment.

Figure 12:
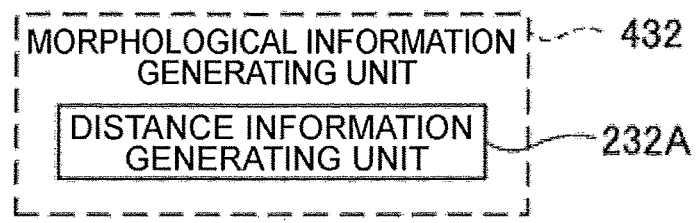
FIG. 12 is a schematic diagram illustrating an example of the configuration of a fundus observation apparatus according to a second modification of the embodiment.

FIG. 12 is a block diagram of an example of the configuration of a morphological information generating unit according to the second modification. In FIG. 12, like reference numerals designate like parts as in FIG. 5, and the same description may not be repeated. Instead of the morphological information generating unit 232 of the data processor 230 illustrated in FIG. 4, a morphological information generating unit 432 illustrated in FIG. 12 can be used.

Figure 13:
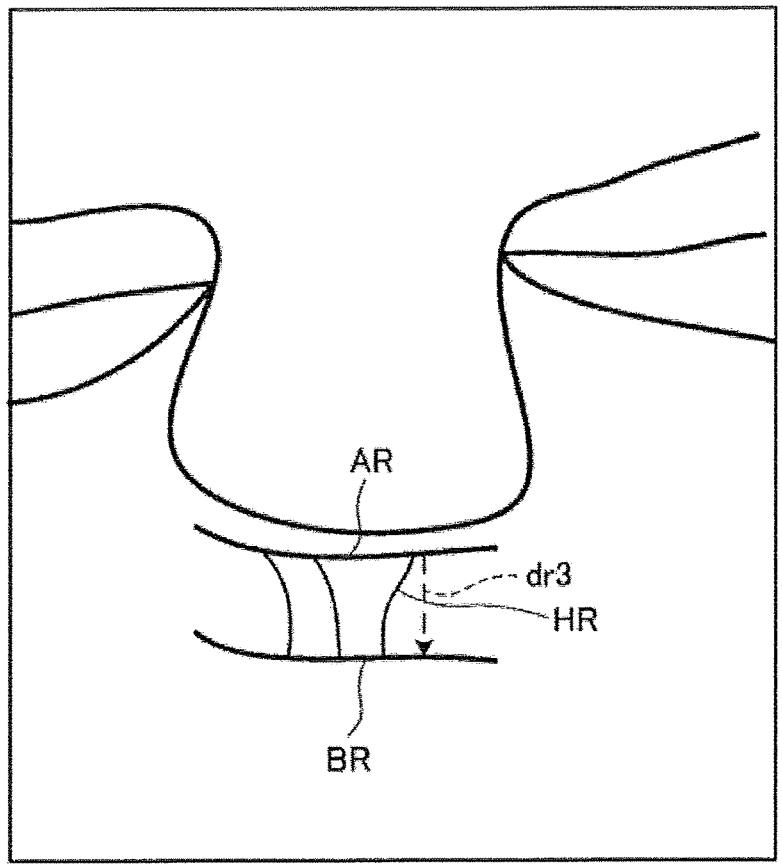
FIG. 13 is a diagram for explaining the operation of the fundus observation apparatus of the second modification of the embodiment.

The morphological information generating unit 432 includes the distance information generating unit 232A. The morphological information generating unit 432 can generate distance information as the morphological information based on a measurement direction set in advance. Examples of the measurement direction set in advance include the vertical direction, i.e., the A-scan direction of OCT (e.g., z-direction in the B-scan image rendering the morphology of the xz plane or the yz plane). The morphological information generating unit 432 generates morphological information using the vertical direction as a measurement direction dr3 as illustrated in FIG. 13.

As described above, according to the second modification, it is possible to obtain the morphological information indicating the morphology of the lamina cribrosa with respect to a direction set in advance. Thus, as in the above embodiment, it is possible to contribute to the evaluation and diagnosis of glaucoma as well as presymptomatic diagnosis and the like.

Third Modification

As described in the above embodiment or the modifications thereof, it is required to set the measurement direction to generate the distance information. According to a third modification of the embodiment, the measurement direction can be changed. Specifically, the third modification is given by an example, in which there is a plurality of setting modes for measurement directions, and the same setting mode as in the previous case can be automatically applied to the trend analysis or the like.

The fundus observation apparatus of the third modification has basically a similar configuration to that of the fundus observation apparatus of the above embodiment. In the following, the fundus observation apparatus of the third modification is described focusing on the differences from that of the above embodiment.

Figure 14:
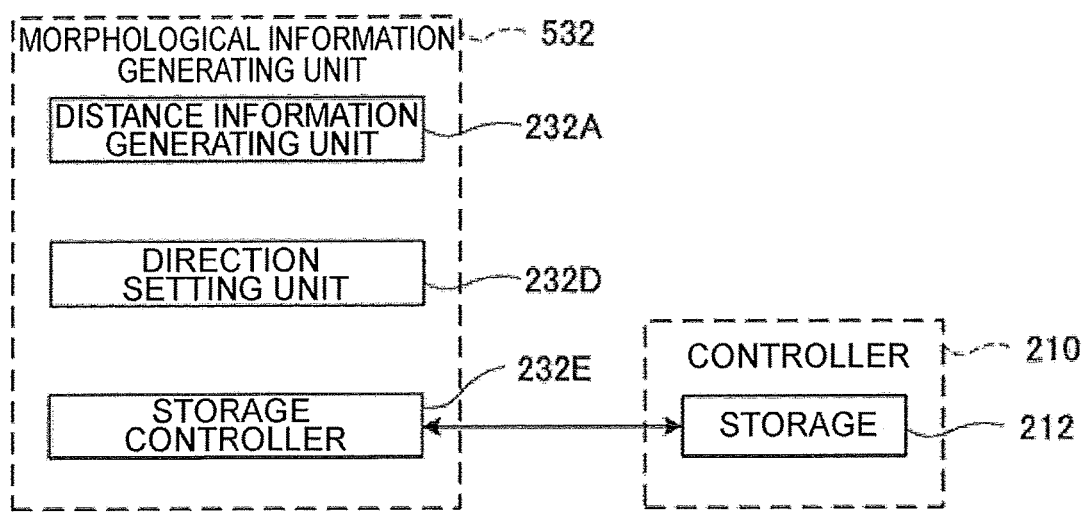
FIG. 14 is a schematic diagram illustrating an example of the configuration of a fundus observation apparatus according to a third modification of the embodiment.

FIG. 14 is a block diagram of an example of the configuration of a morphological information generating unit according to the third modification. FIG. 14 also illustrates the controller 210. In FIG. 14, like reference numerals designate like parts as in FIG. 4, and the same description may not be repeated. As the morphological information generating unit 232 of the data processor 230 illustrated in FIG. 4, a morphological information generating unit 532 illustrated in FIG. 14 can be used.

The morphological information generating unit 532 includes the distance information generating unit 232A, a direction setting unit 232D, and a storage controller 232E. The morphological information generating unit 532 may further include the normal direction specifying unit 232B or the image area specifying unit 232C. The direction setting unit 232D selects one from a plurality of direction setting modes to set the direction for an OCT image stored in the storage 212. The storage controller 232E stores morphological information generated based on the direction setting mode selected by the direction setting unit 232D in the storage 212 (storage means) in association with identification information that identifies the direction setting mode. When a new OCT image is to be analyzed, the direction setting unit 232D retrieves morphological information related to the subject's eye stored by the storage controller 232E in the past, and acquires identification information associated with the morphological information. The direction setting unit 232D then selects and sets the direction setting mode indicated by the identification information acquired, thereby setting the direction for the new OCT image. The distance information generating unit 232A generates distance information indicating the distance between the front area and the rear area in the newly set direction.

As described above, according to the third modification, it is possible to obtain the morphological information indicating the morphology of the lamina cribrosa with respect to the same measurement direction as in the previous case from among a plurality of measurement directions. Thus, as in the above embodiment, it is possible to contribute to the evaluation and diagnosis of glaucoma as well as presymptomatic diagnosis and the like.

Fourth Modification

For example, in step S3 of FIG. 6, the morphological information generating unit may generate morphological information about the lamina cribrosa in a cross section in an arbitrary direction. The cross section in an arbitrary direction is obtained by, for example, arbitrarily setting a cross section to volume data or stack data.

Examples of the cross section in an arbitrary direction include a cross section (C-scan image surface) in the horizontal direction, a plane perpendicular to the normal direction of the front area or the rear area of the lamina cribrosa, a plane perpendicular to the extending direction of the holes of the lamina cribrosa, a plane parallel to the front area or rear area of the lamina cribrosa, and the like.

The normal direction of the front area or the rear area can be specified by, for example, applying a known curved surface approximation to the front area or the rear area to obtain an approximate curved surface, and obtaining the normal direction at an arbitrary measurement point in the approximate curved surface. Alternatively, by applying a known curved surface approximation to the front area or the rear area rendered in a B-scan image to obtain an approximate curve, the normal direction at an arbitrary measurement point in the approximate curve may be obtained as the normal direction of the front area or the rear area. Further, by applying a known curved surface approximation to the front area or the rear area of the lamina cribrosa in an arbitrary three-dimensional area to obtain an approximate curved surface, the normal direction at an arbitrary measurement point in the approximate curved surface may be obtained as the normal direction of the front area or the rear area.

In addition, by applying a known curved surface approximation to the boundary or the end point of the inner limiting membrane (ILM), the nerve fiber layer (NFL), the Bruch's membrane opening (BMO), or the contour of the optic disc to obtain an approximate curved surface, a normal direction from among those in the approximate curved surface, which passes through the measurement point may be used as the normal direction of the front area or the rear area.

Examples of the extending direction of the holes of the lamina cribrosa include the orientation of an image area corresponding to a hole of the lamina cribrosa specified on the basis of the pixel values of a tomographic image generated from the OCT image.

Examples of the morphological information of the fourth modification include the inclination of the front area, the rear area, and the side area of the lamina cribrosa, the inclination of the lamina cribrosa, the distance between the front area and the rear area in a predetermined direction, the curvature of the front area, the curvature of the rear area, the area of the side area, the distribution of the holes, parameters for the shape of the analysis target area and the lamina cribrosa area, and the like. Examples of information indicating the distribution of the holes include the number of the holes, thickness, area, extending state, the major axis and the minor axis of an approximate ellipse that approximates the holes, and the inclination of the major axis and the minor axis, and the like. Examples of the parameters for the shape of the lamina cribrosa area and the analysis target area include the major axis and the minor axis of an approximate ellipse that approximates the areas, the inclination of the major axis and the minor axis, the area of the approximate ellipse, and the like.

Fifth Modification

Figure 15:
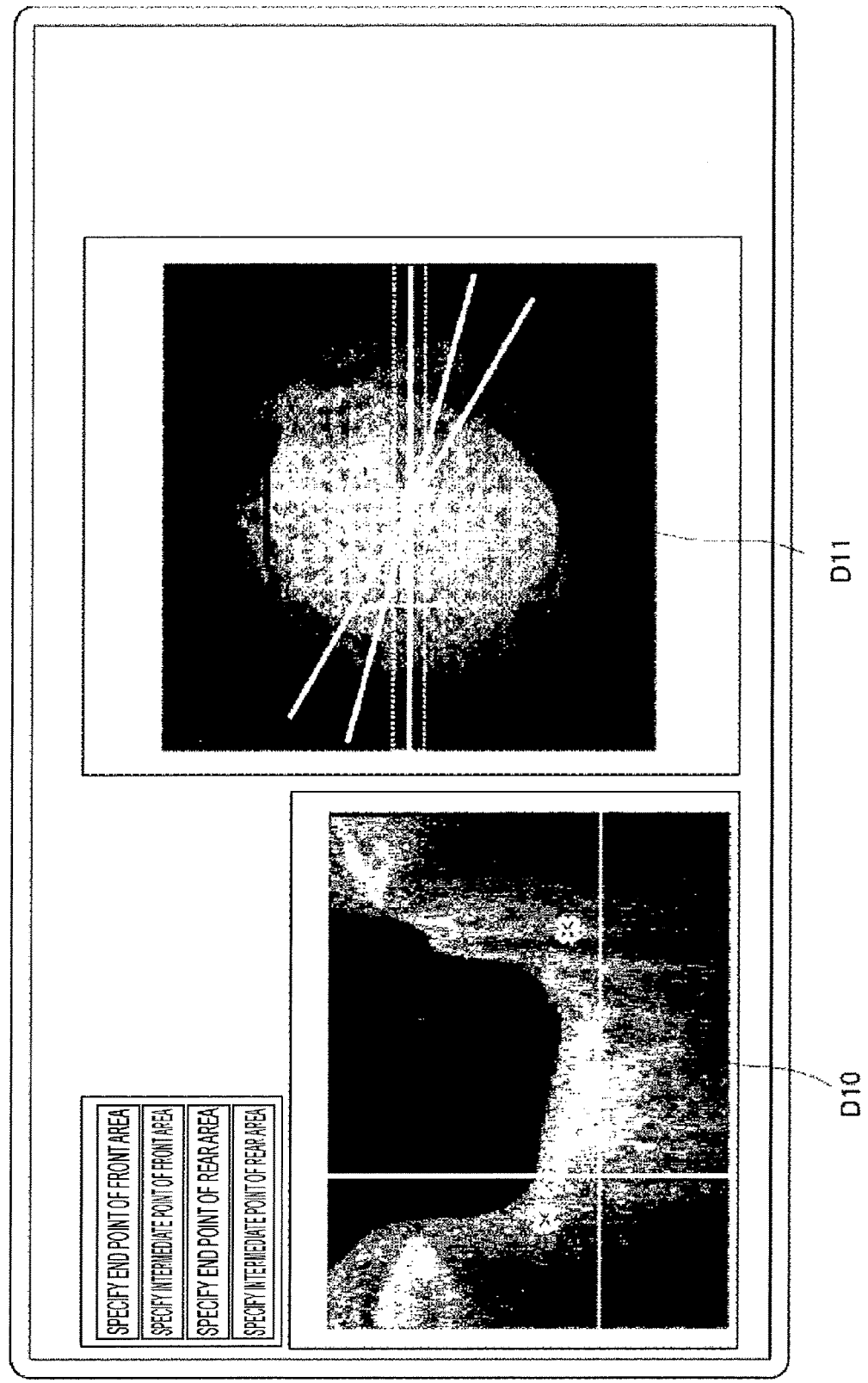
FIG. 15 is a diagram for explaining the operation of the fundus observation apparatus of a fifth modification of the embodiment.

The cross-sectional image data forming unit 230B may be configured to form cross-sectional image data passing through an arbitrary point (measurement point) in a three-dimensional tomographic image based on three-dimensional image data formed by the three-dimensional image data forming unit 230A, and to form an MPR image. Examples of the arbitrary point in a three-dimensional tomographic image include the center of the papilla and the center of BMO of the fundus. Examples of the MPR image include a radial tomographic image centering on the arbitrary point. As the OCT information, the cross-sectional image data forming unit 230B can form a tomographic image representing one or more cross sections that pass through a predetermined measurement point(s) in the fundus. As illustrated in FIG. 15, the image display controller 214 displays a tomographic image (D10) based on the cross-sectional image data formed by the cross-sectional image data forming unit 230B and a C-scan image (D11) formed as above side by side on the display 240A. The area setting unit 231A can set the front and rear areas for an image displayed on the display 240A based on a position specified through the operation unit 240B.

In this manner, the area setting unit 231A can set the front and rear areas for a tomographic image obtained by reconstructing a three-dimensional image (FIG. 15) as well as a raster image such as a B-scan image (FIG. 7) based on a position specified through the operation unit 240B.

Other Modifications

In the above embodiment or the modifications thereof, an example is described in which OCT is applied to the fundus; however, they are not so limited. For example, the embodiment and the modifications can be applied to the case where OCT is applied to the anterior eye segment to analyze a predetermined portion thereof.

In the above embodiment or the modifications thereof, an example is described in which an OCT image is used as OCT information; however, they are not so limited. As described above, the OCT information may be information that has been obtained by OCT and yet to be imaged. Examples of information to be imaged include an FFT processing result (reflection intensity profile) that is based on a detection result obtained by a detector for detecting interference light by using OCT (e.g., detection signal from the CCD image sensor). Therefore, by detecting a peak position (z position) in the FFT processing result, a site or an area in A-scan lines can be specified from, for example, clinical data. Thus, it is possible to specify a desired area (layer), such as the front area of the lamina cribrosa, the lamina cribrosa area, the rear area of the lamina cribrosa, and the like.

A computer program for realizing the above embodiment or the modifications thereof may be stored in an arbitrary recording medium that is readable by a computer. Examples of the recording medium include a semiconductor memory, an optical disk, a magneto-optical disk (CD-ROM, DVD-RAM, DVD-ROM, MO, etc.), a magnetic storage medium (hard disk, floppy (registered trade mark) disk, ZIP, etc.), and the like. The computer program may be sent/received through a network such as the Internet or LAN.

The configurations described above are mere examples for embodying or carrying out the present invention, and therefore susceptible to several modifications and variations (omission, substitution, addition, etc.), all coming within the scope of the invention.

EXPLANATION OF SYMBOLS

1 Fundus observation apparatus
200 Arithmetic and control unit
212 Storage
231A Area setting unit
232, 332, 432, 532 Morphological information generating unit

The invention claimed is:

1. A fundus analysis apparatus, comprising:
a memory that stores OCT information acquired by applying optical coherence tomography to a fundus of an eye; and
a processing circuitry configured to:
set a front area corresponding to a front surface of a lamina cribrosa and a rear area corresponding to a rear surface of the lamina cribrosa in the OCT information,
specify an image area that corresponds to an orientation of holes of the lamina cribrosa based on the OCT information, the orientation of the holes determined in accordance with a (i) B-scan image of the lamina cribrosa and (ii) an approximation of a direction of the holes from the front surface to the rear surface, and
generate morphological information indicating the holes of the lamina cribrosa based on at least (i) the front area, (ii) the rear area, and (iii) the orientation of the specified image area.

2. The fundus analysis apparatus according to claim 1, wherein the processing circuitry is further configured to generate distance information indicating distance between the front area and the rear area as the morphological information.

3. The fundus analysis apparatus according to claim 1, wherein the processing circuitry is further configured to set an area in the OCT information including at least the front area and the rear area as an analysis target area,
wherein the processing circuitry is further configured to generate the morphological information based on the analysis target area set by the processing circuitry.

4. The fundus analysis apparatus according to claim 1, wherein
the OCT information includes a two-dimensional or three-dimensional data set, and
the processing circuitry is further configured to generate distribution information of a parameter indicating the holes of the lamina cribrosa based on the data set as the morphological information.

5. The fundus analysis apparatus according to claim 4, wherein the OCT information includes a tomographic image generated based on the three-dimensional data set.

6. The fundus analysis apparatus according to claim 5, wherein the OCT information includes at least one tomographic image representing at least one cross section that passes through a predetermined measurement point in the fundus.

7. The fundus analysis apparatus according to claim 4, further comprising a display controller configured to display the distribution information on a display according to values of the parameter.

8. The fundus analysis apparatus according to claim 1, wherein
the processing circuitry is further configured to specify a normal direction of the front area or the rear area, and
the processing circuitry is further configured to generate the morphological information based on the normal direction specified by the processing circuitry.

9. The fundus analysis apparatus according to claim 1, wherein the processing circuitry is further configured to generate the morphological information based on an A-scan direction of the optical coherence tomography.

10. The fundus analysis apparatus according to claim 1, wherein
the processing circuitry is further configured to:
select one of a plurality of direction setting modes to set a direction for the OCT information, and
store the morphological information generated based on the selected direction setting mode in the memory in association with identification information that identifies the direction setting mode, and
in response to a determination that new OCT information is to be analyzed, the processing circuitry is further configured to retrieve the identification information associated with the previously stored morphological information, and select and set the direction setting mode identified by the retrieved identification information, thereby setting a direction for the new OCT information.

11. The fundus analysis apparatus according to claim 1, further comprising:
an image display controller configured to display an image based on the OCT information on a display
wherein the processing circuitry is further configured to set at least one of the front area and the rear area based on a specified position with respect to the image displayed on the display.

12. A fundus observation apparatus, comprising
an OCT information generating unit configured to generate the OCT information by applying optical coherence tomography to the fundus of the eye; and
the fundus analysis apparatus according to claim 1.

* * * * *